(12) United States Patent
Selvaraj et al.

(10) Patent No.: US 12,004,852 B2
(45) Date of Patent: Jun. 11, 2024

(54) SENSOR CALIBRATION CONSIDERING SUBJECT-DEPENDENT VARIABLES AND/OR BODY POSITIONS

(71) Applicant: Vital Connect, Inc., San Jose, CA (US)

(72) Inventors: Nandakumar Selvaraj, San Jose, CA (US); Thang Tran, San Jose, CA (US); Arshan Aga, San Jose, CA (US)

(73) Assignee: Vital Connect, Inc., San Jose, CA (US)

( * ) Notice: Subject to any disclaimer, the term of this patent is extended or adjusted under 35 U.S.C. 154(b) by 744 days.

(21) Appl. No.: 15/718,560

(22) Filed: Sep. 28, 2017

(65) Prior Publication Data

US 2019/0090781 A1    Mar. 28, 2019

(51) Int. Cl.
*A61B 5/11* (2006.01)
*A61B 5/00* (2006.01)
*A61B 5/024* (2006.01)
*G01P 21/00* (2006.01)

(52) U.S. Cl.
CPC ............ *A61B 5/11* (2013.01); *A61B 5/02416* (2013.01); *A61B 5/1116* (2013.01); *A61B 5/1121* (2013.01); *A61B 5/6833* (2013.01); *G01P 21/00* (2013.01); *A61B 5/024* (2013.01); *A61B 2560/0223* (2013.01); *A61B 2562/0219* (2013.01)

(58) Field of Classification Search
CPC .............................. A61B 5/11; A61B 5/02416
USPC .......................................... 702/104
See application file for complete search history.

(56) References Cited

U.S. PATENT DOCUMENTS

| | | | | |
|---|---|---|---|---|
| 2011/0048103 A1* | 3/2011 | Su | ............ | G01C 21/16 73/1.79 |
| 2011/0201969 A1* | 8/2011 | Hatlestad | ............ | A61B 5/1118 600/587 |
| 2011/0238355 A1* | 9/2011 | Hara | ............ | H01Q 3/267 702/104 |
| 2013/0179108 A1* | 7/2013 | Joseph | ............ | G01D 18/00 702/104 |
| 2014/0019080 A1* | 1/2014 | Chan | ............ | A61B 5/1118 73/1.37 |
| 2014/0372063 A1* | 12/2014 | Niu | ............ | G01C 25/005 702/141 |
| 2016/0296159 A1* | 10/2016 | Larson | ............ | A61G 7/057 |
| 2016/0302715 A1 | 10/2016 | Larson | | |
| 2017/0027498 A1* | 2/2017 | Larson | ............ | A61B 5/447 |
| 2017/0184630 A1 | 6/2017 | Chan | | |

FOREIGN PATENT DOCUMENTS

WO     2016/088842 A1    6/2016

OTHER PUBLICATIONS

European Extended Search Report from EP Application No. 18860291.6 dated May 25, 2021, 8 pages.

* cited by examiner

*Primary Examiner* — Ricky Go
(74) *Attorney, Agent, or Firm* — Shih IP Law Group, PLLC

(57) ABSTRACT

A system, device and method of calibrating a sensor determine a sensor vector associated with a subject; process the sensor vector; determine a sensor elevation angle as a prediction of the subject's body elevation from a result of processing the sensor vector; and perform calibration using the sensor vector, sensor elevation angle, and a gravity vector.

16 Claims, 14 Drawing Sheets

SENSOR CALIBRATION CONSIDERING SUBJECT-DEPENDENT VARIABLES AND/OR BODY POSITIONS

TECHNICAL FIELD

The present disclosure relates to performing calibration of a sensor attached to a subject (such as a patient) while lying in supine with or without tilting of a surface (such as a bed) supporting the subject, and more particularly, to determining a sensor elevation angle according to the subject's body elevation during the calibration process, performing alignment of the sensor with reference to the body and gravity, detecting true changes in relative body angle or posture of the subject, and accurate assessment of physiological and other physical related measures of the subject.

BACKGROUND

Wireless sensor devices have been increasingly used to monitor subjects including patients in hospitals or users at home. In addition to monitoring of vital signs and physiological measures, wireless sensor devices may be useful for tracking changes in relative body positions of a subject for various applications, including assessment of body position/posture patterns during the day or at night, or preventive management of bedsores in patients, for example. In order to objectively assess relative body positions (or postures) of the subjects, for example, the sensor may require calibration, a process that allows alignment of the sensor device frame to the subject's body frame with reference to gravity.

If proper calibration of the sensor is not performed, accurate posture detection from information provided by a subject-mounted sensor (e.g., an accelerometer) may be challenging, in part because the sensor may be attached in different locations (or sites) on the subject's body and/or with different orientations relative to the subject (e.g., a patient) or associated support (e.g., a bed, particularly a hospital bed that can be adjusted to different elevations based on treatment, procedure and recovery stage), making it potentially difficult to distinguish postures using data acquired from a non-calibrated sensor.

Calibration data may be obtained from a standardized attachment of a sensor at a particular location and orientation on the subject's body and at a standardized relative body position, such as supine with no body elevation during calibration. Strictly adhering to the standardized precise location or orientation of the sensor on the body and the desired body position for calibration process, such as supine at 0° body elevation, are practically not achievable due to variations in body contour (among individuals of different gender and body-mass index, for example), human error in carrying out sensor attachment procedures, and noncompliance with ideal body position during calibration due to such factors as disease conditions, ailments and clinical treatments that may require the subject to remain in bed at certain bed elevations (e.g., 30°).

Therefore, there is a need for a sensor system that allows performing calibration by overcoming practical limitations when the patient or user is in upright vs supine (and in case of supine, with or without body elevation), and that enables accurate assessment of relative body positions.

SUMMARY

A method, device, and system for performing calibration of a sensor attached to a subject while lying in supine, with or without tilting of a supporting surface, that can enable accurate tracking of relative body position is presented.

In a first aspect, a method of calibrating a sensor associated with a subject comprises: attaching the sensor to a portion of the subject; positioning the portion of the subject at a first elevation angle relative to a reference; activating the sensor to produce a sensor vector $\vec{V}$ associated with body acceleration of the subject relative to a gravity vector; calibrating the sensor vector $\vec{V}$, including: processing the sensor vector $\vec{V}$ with the subject at the first elevation angle to produce a first calibrated sensor vector $\vec{V}_S$, determining a second elevation angle $\eta$ associated with elevation of the subject relative to the reference, and calibrating the first calibrated sensor vector $\vec{V}_S$ using the second elevation angle $\eta$ to produce a second calibrated sensor vector $\vec{V}_{S\eta}$; and determining a physiological or physical assessment of the subject using the second calibrated sensor vector $\vec{V}_{S\eta}$.

In a second aspect, a system to calibrate a sensor associated with a subject comprises: a processor and a memory device coupled to the processor, wherein the memory device includes an application that, when executed by the processor, causes the processor to: determine a sensor vector $\vec{V}$ associated with body acceleration of the subject relative to a gravity vector; calibrate the sensor vector $\vec{V}$, including: processing the sensor vector $\vec{V}$ with the subject at a first elevation angle relative to a reference to produce a first calibrated sensor vector $\vec{V}_S$, determining a second elevation angle $\eta$ associated with elevation of the subject relative to the reference, and calibrating the first calibrated sensor vector $\vec{V}_S$ using the second elevation angle $\eta$ to produce a second calibrated sensor vector $\vec{V}_{S\eta}$; and determine a physiological or physical assessment of the subject using the second calibrated sensor vector $\vec{V}_{S\eta}$.

In a third aspect, a sensor device comprises: one or more sensors, a structure configured to support the one or more sensors for attachment to the subject, a processor, and a memory device coupled to the processor, wherein the memory device includes an application that, when executed by the processor, causes the processor to: determine a sensor vector $\vec{V}$ associated with body acceleration of the subject relative to a gravity vector; calibrate the sensor vector $\vec{V}$, including: calibrating the sensor vector $\vec{V}$ with the subject at a first elevation angle relative to a reference to produce a first calibrated sensor vector $\vec{V}_S$, determining a second elevation angle $\eta$ associated with elevation of the subject relative to the reference, and calibrating the first calibrated sensor vector $\vec{V}_S$ using the second elevation angle $\eta$ to produce a second calibrated sensor vector $\vec{V}_{S\eta}$; and determine a physiological or physical assessment of the subject using the second calibrated sensor vector $\vec{V}_{S\eta}$.

DETAILED DESCRIPTION

Figure 1:
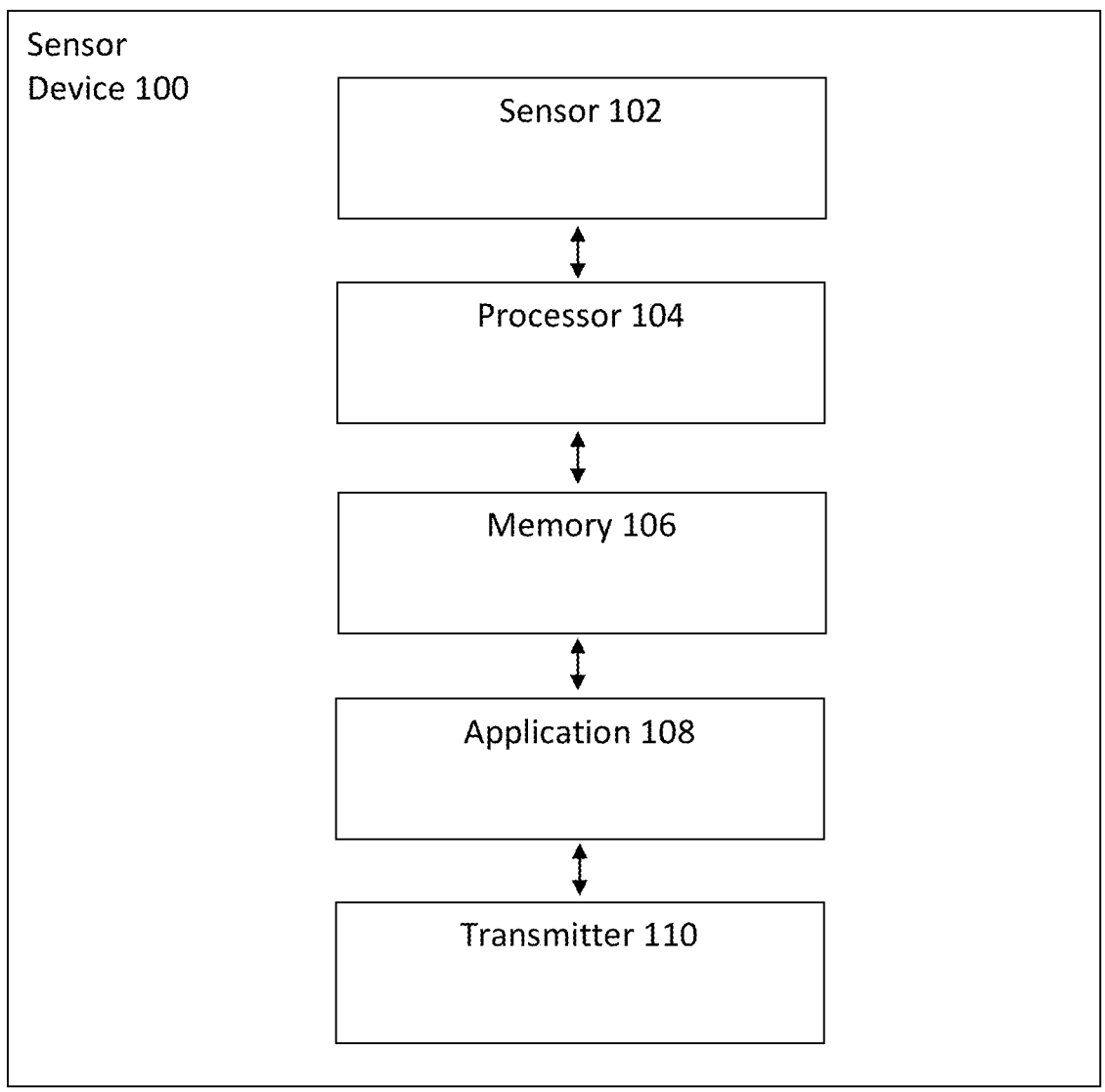
FIG. 1 illustrates a sensor device in accordance with one or more embodiments.

The present disclosure relates to performing sensor calibration and, more particularly, to a method, device, and system to determine an elevation angle of a sensor device attached to a subject while lying in supine with or without tilting of a supporting surface such as a bed, to performing alignment of a sensor device frame to a subject's body frame with reference to gravity, and to detecting true changes in relative body angle or posture of the subject. Examples of the sensor device may include, but are not limited to, one or more of a wearable sensor device, a wired or wireless sensor device, and a sensor device that may incorporate both wired and wireless features. In one or more embodiments, a wired and/or wireless sensor device may be wearable, in whole or in part. The sensor device may incorporate sensing of any physiological variable, including but not limited to physiological signals such as electrocardiogram (ECG) and photoplethysmogram (PPG), or any physical body motion (using, e.g., accelerometry).

In the present description, the terms in at least the following combinations, though potentially differentiable by one of ordinary skill in the art, may be used substantially interchangeably for convenience except as noted: "measurement", "detection" and "monitoring"; "posture", and "body-position", "location", "position" and "orientation"; "sensor" and "sensor device" (although, in general, a sensor device is intended to include a sensor); "attach", "place" and "mount"; "subject", "patient" and "user"; and "determine", "calculate", "compute" and "derive".

One or more embodiments disclosed herein are presented in the context of a calibrating a sensor attached to a patient in bed. Such embodiments are illustrative and not intended to be limited by the context.

The following description is presented to enable one of ordinary skill in the art to make and use the disclosed embodiments and modifications thereof, and is provided in the context of a patent application and its requirements. Various modifications to the disclosed embodiments and the principles and features described herein will be readily apparent to those of ordinary skill in the art. Thus, the present disclosure is not intended to limit the invention to the embodiments shown; rather, the invention is to be accorded the widest scope consistent with the principles and features described herein.

A sensor designed to measure physiological or physical variables of a subject may require calibration, a process that allows the sensor to capture certain conditions (e.g. initial) or adjust certain variables and customize the sensor outputs according to the given individual. One or more embodiments in the present disclosure may be related to calibration of the sensor in measuring a body acceleration of a subject (including acceleration of the body or any part thereof) and measuring physiological/physical variables such as respiration, body posture, step count, core body activity and fall detection using, for example, an accelerometer or a microelectromechanical system (MEMS), which may include an accelerometer.

Performing a sensor calibration process can be very complex to simple depending on requirements, assumptions and inputs. If the sensor is allowed to be attached to a user in different combinations of locations and/or orientations, the sensor may require a calibration procedure that can standardize the measurement conditions and processes by aligning the sensor or sensor frame to the subject's body frame with reference to gravity. Furthermore, a calibration procedure may enable rotation of three axes of an acceleration sensor in order to line up with predefined or desired or "actual" body axes. For example, non-calibrated tri-axial accelerometer data can be arbitrarily positioned relative to the body axes.

A sensor that only utilizes non-calibrated data may lead to less accurate monitoring of body postures and core body activity levels. On the other hand, calibration allows alignment of a tri-axial sensor-frame to the subject's body-frame (e.g., with y pointing to the "head", z pointing to the posterior, and x pointing right-to-left), and enables detecting true changes in relative body angles such as vertical body angle (θ), an angle between the calibrated sensor-Y axis and the negative gravity vector, according to one or more embodiments, and can provide accurate monitoring of body postures, core body activity levels, and physiological signals associated with, e.g., respiration.

Sensor calibration methods can differ broadly based on the location and orientation of the sensor attachment on the subject, the desired body position of the subject during the calibration process and inputs related to sensor location and body position. One or more embodiments in the present disclosure may be more related to performing sensor calibration when the subject's body position is in supine with or without tilting of a supporting surface, such as a bed.

Bed elevation or head-of-bed elevation is prescribed for some patients in hospitals. Bed position or elevation may be a critical factor in determining patient outcome. For example, sitting upright can be very harmful in stroke patients leading to cessation of blood flow and oxygen to the brain. On the other hand, lying flat can increase the intracranial pressure and potentially cause damage to the brain. Therefore, a tolerable level of bed elevation is commonly used in stroke patients. In another example, patients receiving mechanical ventilation (with endotracheal intubation) and tube feedings are recommended to have a bed elevation between 30° and 45° that can help to prevent aspiration and reduce risks of developing aspiration pneumonia (or ventilator-associated pneumonia). In addition to such specific group of patients, a flat supine position on the bed may not be practical or be the most comfortable position in general. Bed position or elevation may be a useful variable for other reasons as well.

Therefore, monitoring of patients in hospitals in elevated bed conditions is common. A wearable sensor device useful in monitoring a patient in elevated bed settings may benefit from calibration in order to provide physiological and physical variables accurately. One or more embodiments disclosed herein first present a "Calibration in Supine Algorithm" for performing sensor calibration with the subject lying flat or supine on a bed or other supporting surface by determining a sensor vector of body acceleration relative to gravity, determining a plurality of rotations to align the sensor device frame to the subject's body frame using the sensor vector and gravity vector, and determining the calibrated sensor vector by the product of the rotational matrix and the sensor vector. However, performing this method by itself may not be as accurate as desired if there will be a bed elevation involved.

To overcome limitations of the Calibration in Supine Algorithm and to perform calibration in bed elevation conditions, this disclosure presents a "Calibration with Sensor Angle Algorithm" and a "Calibration with Bed Angle Algorithm," either or both methods of which may be used in conjunction with the Calibration in Supine Algorithm. In the Calibration with Sensor Angle Algorithm, a sensor elevation angle may be determined automatically while accounting for body contour and the tilting of the supporting surface using a captured sensor vector of body acceleration relative to gravity during the calibration process. The Calibration with Bed Angle Algorithm may obtain user input of body elevation angle. Then, using either the automatically determined sensor elevation angle or the user-inputted body elevation angle, both methods may determine a plurality of rotations to align the sensor device frame to the body frame using the sensor vector, sensor/body elevation angle and gravity vector; and determine the calibrated sensor vector by the product of a rotational matrix and the sensor vector. Furthermore, one or more embodiments are described that can automatically determine information on whether the subject is in upright or otherwise not supine.

One of ordinary skill in the art readily recognizes that a variety of sensor devices, including entirely or partially wireless devices, can be utilized including but not limited to a wireless sensor device in a patch form-factor, accelerometers, gyroscopes, and/or pressure sensors within the spirit and scope of the present invention. Examples of accelerometers may include, without limitation, tri-axial accelerometers, uni-axial accelerometers, bi-axial accelerometers, any of which may be MEMS accelerometers.

Various embodiments of sensor elevation angle detection and sensor calibration are set forth in the following description in conjunction with the accompanying Figures.

FIG. 1 illustrates a sensor device 100 for determining sensor elevation angle and performing sensor calibration so as to enable accurate measurement of one or more physiological measurements such as respiration and/or one or more physical measurements such as posture, core body activity, and fall detection in accordance with one or more embodiments. One or more features of the illustrated sensor device may also be applicable to partially wireless and/or wired sensor devices, and thus wireless features of FIG. 1 should not be considered limiting of sensor device 100. Sensor device 100 may include a sensor 102, a processor 104 coupled to sensor 102, a memory 106 coupled to processor 104, an application 108 coupled to memory 106, and a transmitter 110 coupled to application 108 as shown. One of ordinary skill in the art readily recognizes that sensor device 100 can include other components and that components of sensor device 100 can be coupled in a variety of different ways, and such modifications would be within the spirit and scope of the present invention.

In one or more embodiments, sensor device 100 may be attached in any orientation to a subject and on any location of the subject suitable for its purpose. In one or more embodiments, sensor device 100 may be chest-mounted to the subject. Sensor 102 may obtain data from the subject and transmit the data to memory 106 and application 108. Processor 104 may execute application 108 to monitor information regarding the subject's physiological measures including respiration and physical related measures including body posture, core body activity and/or fall detection. The information may be provided to transmitter 110 and in turn transmitted for analysis by a human or another device, or for any other purpose, for instance.

In one or more embodiments, sensor 102 may include any of an embedded sensor with electrodes, an accelerometer and/or optical system, and processor 104 may include a microprocessor. One of ordinary skill in the art readily recognizes that a variety of devices can be utilized for processor 104, memory 106, application 108, and transmitter 110, and that such modifications or details would be within the spirit and scope of the present invention.

In one or more embodiments, a wearable device may have an adhesive patch biosensor worn on the chest that incorporates, e.g., two surface electrodes with hydrogel on the bottom, a battery, an electronic module with an embedded processor or a system-on-chip and other electronic components and circuitry, a MEMS tri-axial accelerometer, optical sensor and a Bluetooth Low Energy (BLE) transceiver. The wearable device may be partly (semi-) disposable, disposable and/or reusable.

In one or more embodiments, the calibration process or procedure may start after sensor device 100 is powered on and is attached to the subject (typically the chest area of a human subject). The calibration process may be repeated every time the sensor device is attached to the subject by initiating manually (e.g., by pressing a button provided on sensor device 102 or providing a signal remotely) or can automatically determine the subject's stable body position such as supine with no elevation, supine with elevation or upright, and calibrate the sensor accordingly.

Figure 2:
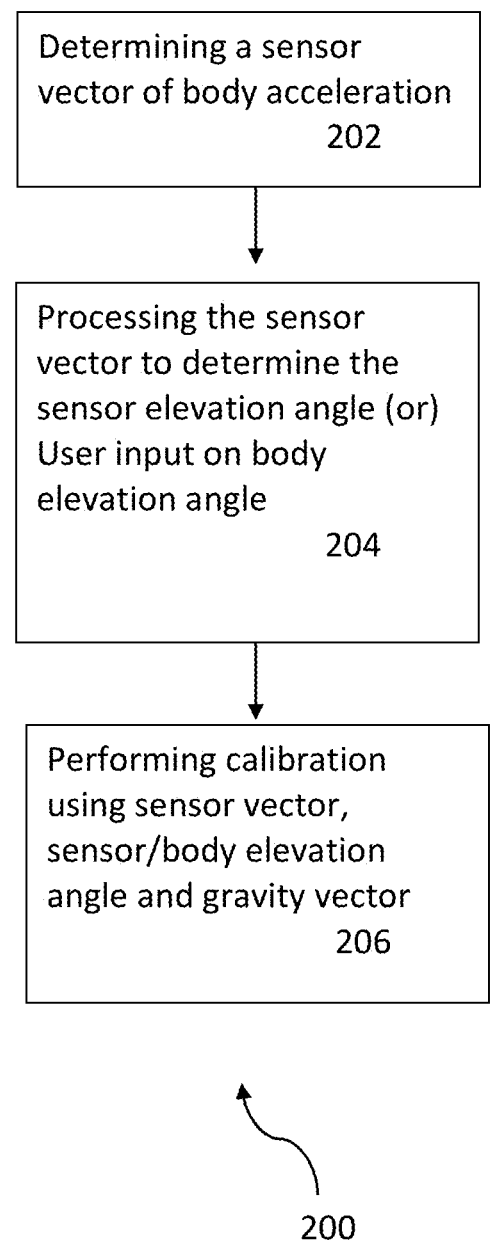
FIG. 2 illustrates a method of performing sensor calibration according to one or more embodiments.

FIG. 2 illustrates a high level example of a method 200 for determining sensor elevation angle and performing sensor calibration using a sensor device such as sensor device 100 according to one or more embodiments. Method 200 involves determining a sensor vector of body acceleration after the sensor is attached on the subject's body in block 202 by initiating manually (e.g., by pressing a button provided on sensor device 102, pressing a button, toggle or tile on a user interface application on a smart phone or tablet, or providing a signal remotely) or by initiating automatically based on the subject's stable body position. In one or more examples, the sensor vector of body acceleration may be determined by any suitable accelerometer, including but not limited to a MEMS, although one or more devices in the art may be used in addition to an accelerometer or in the alternative.

In block 204, the sensor vector is processed to determine the elevation angle of sensor device 100 attached on the subject's body compared to a reference plane such as horizontal (e.g., the earth's surface) in one or more embodiments, or any other plane(s) or direction(s) relative to an established reference frame. Instead of calculating sensor elevation angle, body elevation angle can be input as a substitute variable for calibration process.

In block 206, calibration of sensor device 100 is performed using the sensor vector determined in block 202, the sensor elevation angle determined in block 204 or a body elevation angle input by the subject or another user determined in block 204, and the gravity vector.

Figure 3:
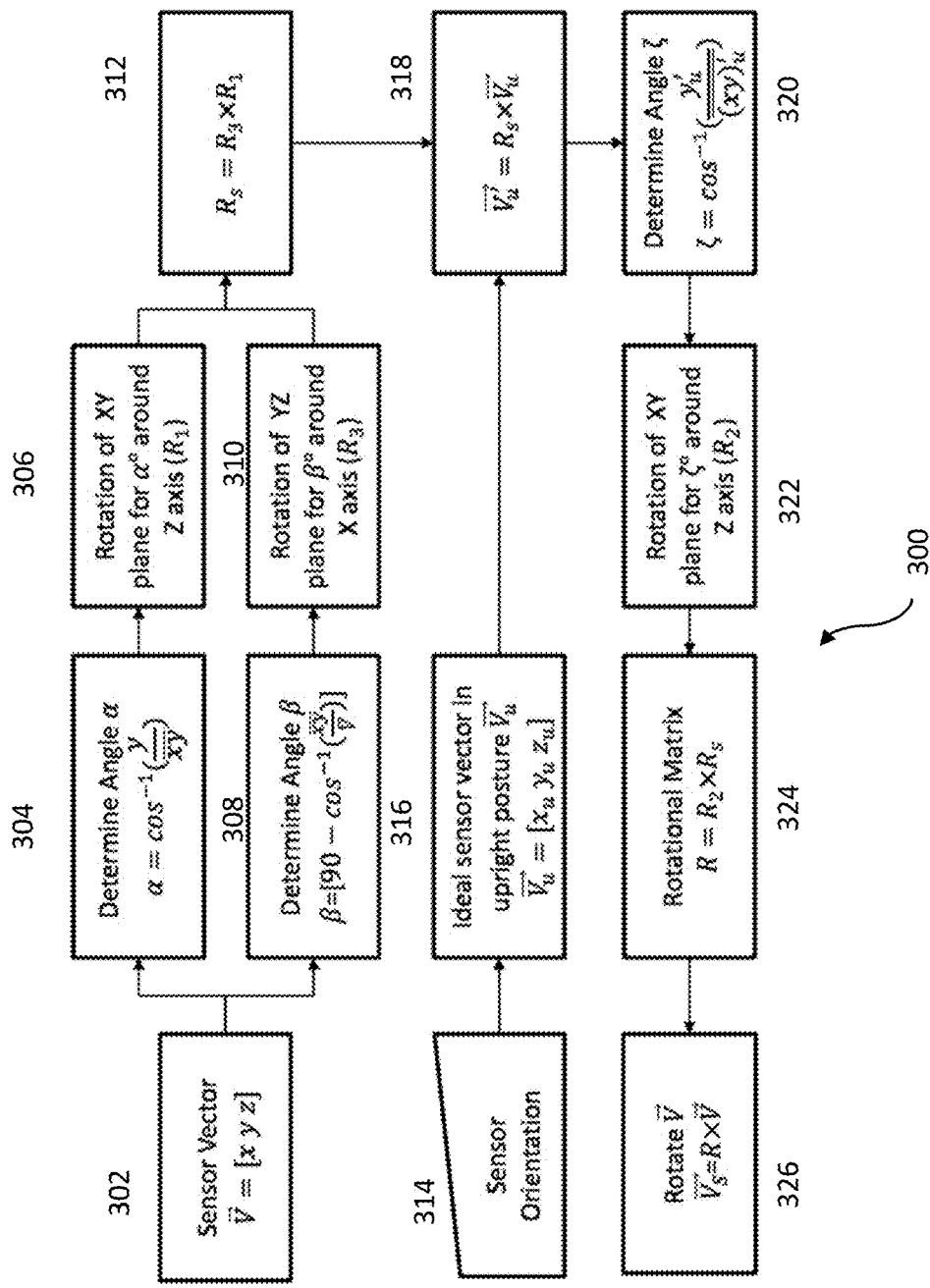
FIG. 3 illustrates an example of a Calibration in Supine Algorithm assuming no sensor/body elevation in accordance with one or more embodiments.

Methods for performing sensor calibration based on one or more factors (e.g., one or more conditions) and user inputs are presented henceforth. The method 300 illustrated in FIG. 3 is an example of a Calibration in Supine Algorithm in which the subject may lie supine on a horizontal supporting surface such as a bed without any tilting, and information on orientation of sensor device 100 attached on the subject is input. The Calibration in Supine Algorithm may assume no sensor/body elevation (required initial condition) during the calibration process in accordance with one or more embodiments.

FIG. 3 illustrates method 300 for the Calibration in Supine Algorithm in accordance with one or more embodiments. In step 302, one sample or an aggregate of samples of body acceleration of the subject's body under stable supine position may be obtained from sensor device 100 as a sensor vector $\vec{V} = [x\ y\ z]$ in accordance with one or more embodiments, where the sensor can be a tri-axial accelerometer and $[x\ y\ z]$ be the acceleration values in three axes. The captured sensor vector may be used to calculate $\alpha$ as an angle between the y axis to the XY plane of the sensor vector per the equation $$\alpha = \cos^{-1}\left(\frac{y}{\overline{xy}}\right)$$

in step 304. With the calculated angle $\alpha$, a rotational matrix $R_1$ may be calculated representing a rotation of the XY plane of the sensor vector for $\alpha°$ around the Z axis. Depending on whether the rotation is applied using the left-hand-rule or the right-hand-rule and sensor configuration, the rotational matrices may differ. An example of $R_1$ can be $[(-\cos \alpha)\ \sin \alpha\ 0;\ \sin \alpha\ \cos \alpha\ 0;\ 0\ 0\ 1]$, according to one or more embodiments.

Likewise, another angle $\beta$ may be calculated using the captured sensor vector by the equation $$\beta = \left[90 - \cos^{-1}\left(\frac{\overline{xy}}{\overline{V}}\right)\right]$$

given in step 308. With the determined angle $\beta$, a rotational matrix $R_3$ may be calculated representing a rotation of the YZ plane of the sensor vector for $\beta°$ around the x axis via step 310. According to one or more embodiments, an example of $R_3$ can be $[1\ 0\ 0;\ 0\ \cos \beta\ (-\sin \beta);\ 0\ \sin \beta\ \cos \beta]$. Using the rotational matrices $R_1$ and $R_3$, an intermediate rotational matrix $R_s$ may be determined as a product of $R_3$ and $R_1$ as in step 312.

In one or more embodiments, method 300 may include an input on sensor orientation, such as whether the sensor device is inclined, parallel or vertical with reference to a midline of the body that symmetrically bisects the body. In step 314, the sensor orientation on the body may be input, for example manually using an input on sensor device 100 or remotely, or by selecting an orientation input on a user interface application on another device such as a smart phone or tablet. According to the sensor orientation input, in step 316, an ideal sensor vector $\vec{V}_u = [x_u\ y_u\ z_u]$ for the subject in an upright posture may be determined. In one or more embodiments, the sensor vector in upright $\vec{V}_u$ can be, for example, any of $[-0.707\ -0.707\ 0]$ or $[0\ -1\ 0]$ or $[-1\ 0\ 0]$ for 45° inclined, parallel and perpendicular sensor orientations with reference to body midline.

In step 318, the product of the intermediate rotational matrix $R_s$ and ideal upright sensor vector $\vec{V}_u$ may be computed to give $\vec{V}'_u$. Now, an angle $\zeta$ may be determined by the equation $$\zeta = \cos^{-1}\left(\frac{y'_u}{(xy)'_u}\right)$$

as given in step 320. With the calculated angle $\zeta$, another rotational matrix $R_2$ may be calculated representing a rotation of the XY plane of the sensor vector for $\zeta°$ around the z axis via step 322. An example of $R_2$ can be $[(-\cos \zeta)\ (-\sin \zeta)\ 0;\ \sin \zeta\ (-\cos \zeta)\ 0;\ 0\ 0\ 1]$, according to one or more embodiments. With the determination of three required different rotations ($R_1$, $R_3$, $R_2$) to calibrate the sensor, a rotational matrix R may be determined by the multiplication of matrices $R_2$ and $R_s$ (where $R_s=R_3 \times R_1$) as in step 324. Using rotational matrix R obtained according to the Calibration in Supine Algorithm, the input sensor vector $\vec{V}$ can be rotated to obtain a calibrated sensor vector $\vec{V}_S$ by the equation $\vec{V}_S=R \times \vec{V}$ as in step 326. Thus, the Calibration in Supine Algorithm as in method 300 allows calibration or alignment of sensor device 100 (e.g., the sensor device frame) to the subject's frame with reference to the gravity vector when the subject is in supine position without any elevation of the lying surface or bed.

After the rotations applied to the sensor vector aligning to the body-frame, the vertical body angle (θ) can be calculated as an angle between the calibrated sensor-Y axis and the upright negative gravity vector $$(\vec{G_u} = [0(-1)0]) \text{ as } \theta = \cos^{-1}\left(\frac{y_s}{\vec{G_u}}\right)$$

according to one embodiment, to assess the relative body angle with reference to $\vec{G_u}$. The calculated vertical body angle (θ) can be further used to determine posture of a subject including upright, upside down, leaning, supine, prone, depending on the magnitude of θ.

Figure 4:
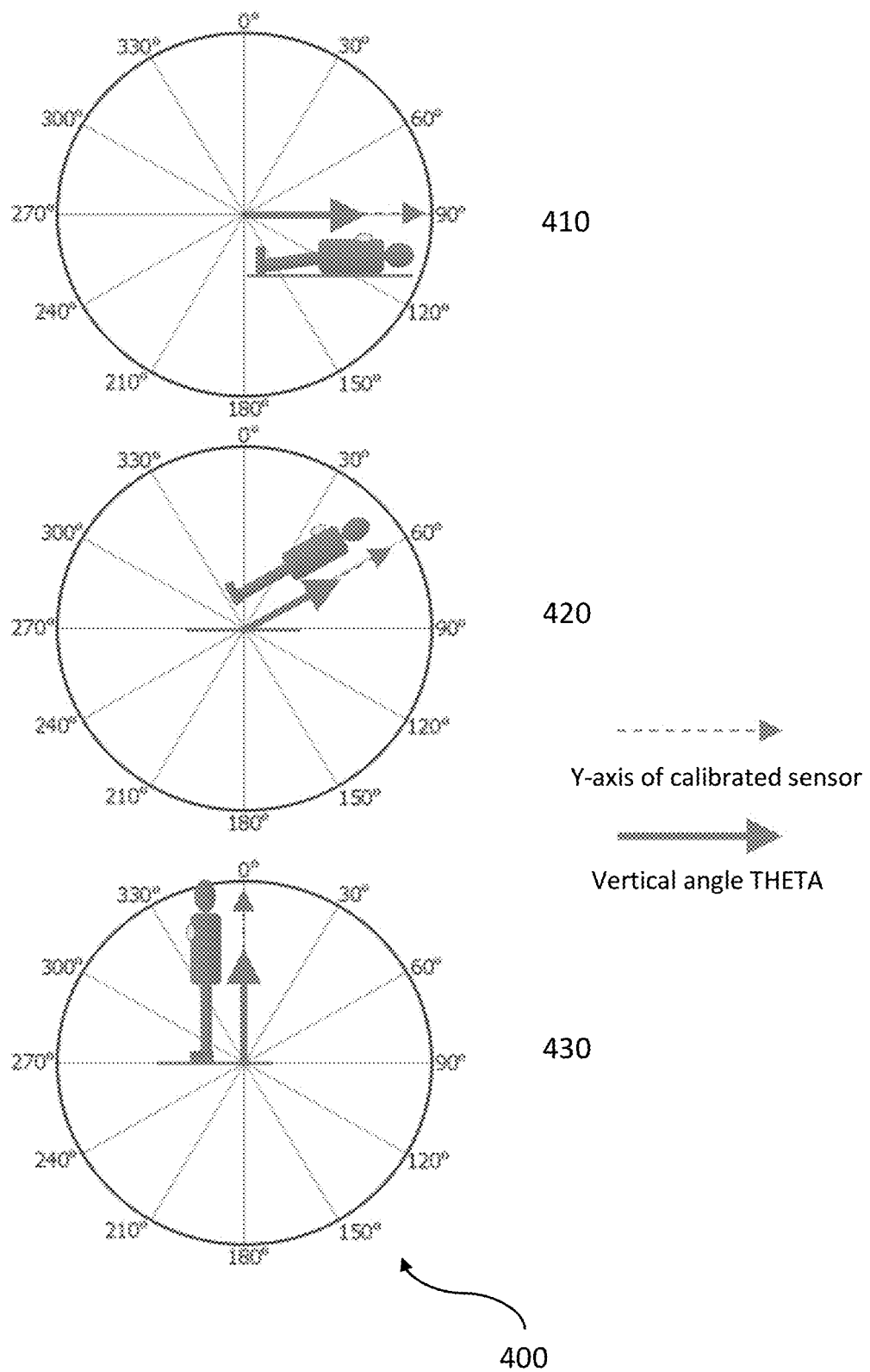
FIG. 4 illustrates ideal examples of a calibrated y component of a sensor vector and a calculated vertical body angle in three body positions—supine (upper panel), leaning (middle panel) and upright (lower panel)—when the Calibration in Supine Algorithm is used to calibrate the sensor assuming no sensor/body elevation.

FIG. 4 illustrates an example of performing calibration of sensor device 100 attached on an "ideal" upper body (e.g., without any body contours) lying supine without any body elevation using method 300. Top panel 410 shows a calibrated y component of the sensor vector (dotted arrow) and calculated vertical body angle θ (solid arrow pointing to the angle on a 360° dial) when the ideal human body is in supine condition without any elevation. After the calibration using method 300 in supine, the θ value may show the body angle as 90° in supine. If the body supporting surface (e.g., bed) is elevated to 30° compared to the horizontal plane as shown at 420 (middle panel), the calibrated y axis and vertical body angle θ indicate a corresponding 30° change in body elevation (i.e., the θ value can be 60° with a change of 30° compared to supine). If the body elevation continues to change into an upright position as in lower panel 430, the calibrated y axis and vertical body angle θ can indicate a corresponding change in 90° body elevation compared to the horizontal plane (i.e., the θ value can be 0° with a change of 90° compared to supine). Thus, the calibration of sensor device 100 may allow tracking of the relative change in relative body angle including vertical body angle θ that can be used to determine posture of a subject.

In contrast to the ideal body without any body contours, the human body is not a rectangular prism or a cylinder in shape but is subject to different sizes and varying shapes with contours of the upper body, for example. Therefore, when sensor device 100 is attached to a typical human body, the sensor device frame may be subjected to a certain elevation (e.g., angular orientation) (up to 20°, for example) depending on gender, body-mass index, attachment site, etc.

Figure 5:
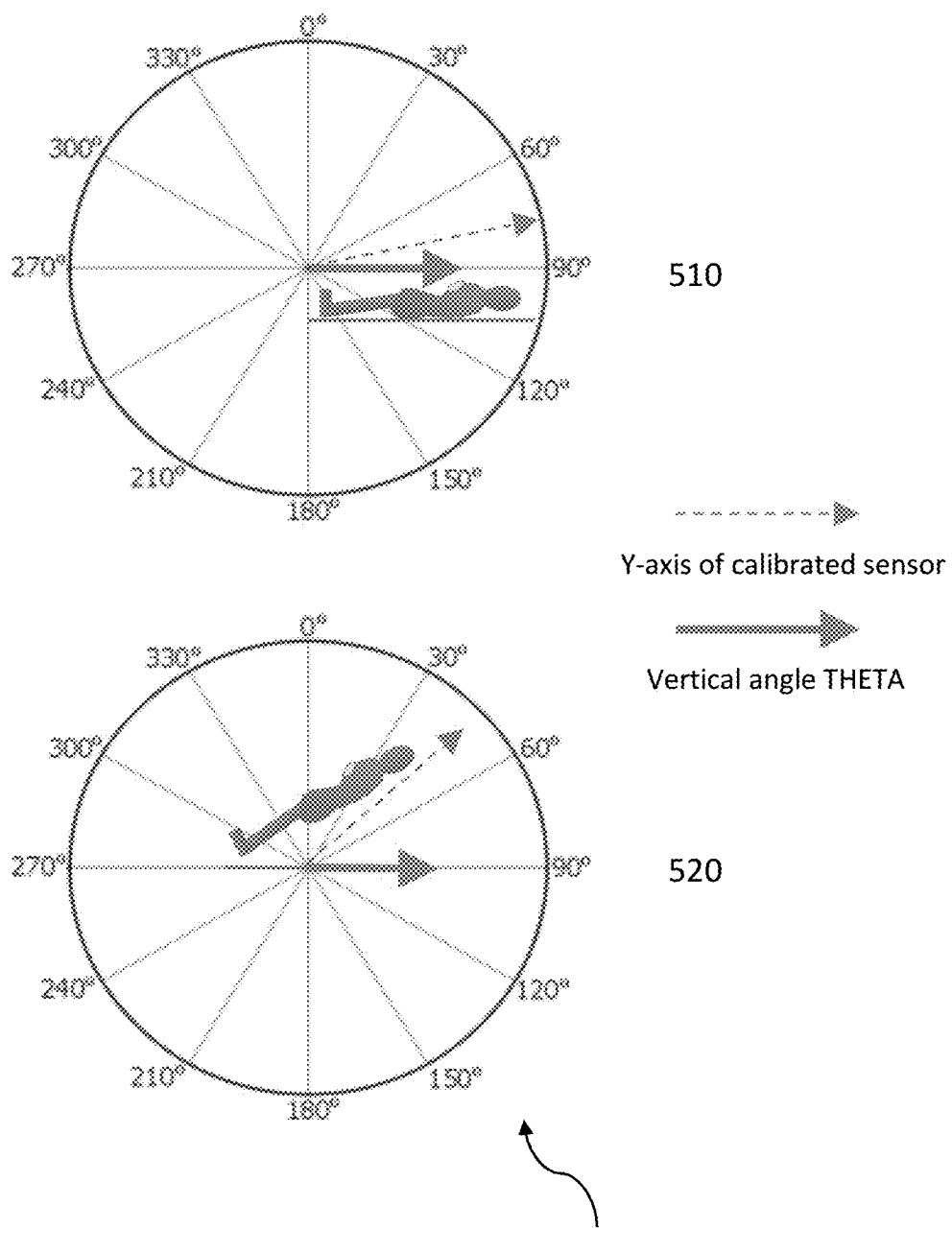
FIG. 5 illustrates practical examples of the calibrated y component of the sensor vector and the calculated vertical body angle when the Calibration in Supine Algorithm is applied to calibrate the sensor in supine position (upper panel) and elevated body position (lower panel) of a subject having a body contour.

For example, as shown in upper panel 510 of FIG. 5, when the subject is lying in supine on a horizontal surface (e.g., bed) without any elevation, sensor device 100 may experience a certain level of elevation (positive or negative relative to the horizontal surface). In such instances, method 300 may not quantify or account for sensor elevation during calibration. For example, sensor elevation due to body contours may be nullified in the vertical body angle θ calculated for supine using method 300, resulting in a value of 90°. Accordingly, the deviation in true relative position of the body in method 300 will be approximately equal to the sensor elevation angle caused by body contour(s). But, if the same method 300 is applied to calibrate sensor device 100, and the subject is not in 0° bed elevation (supine) but applied with a considerable bed elevation such as 45°, as shown in lower panel 520 of FIG. 5, the relative body angle can be highly erroneous. For example, the vertical body angle can be quantified as 90° instead of a true relative body angle of 45°. Thus, applying method 300 for elevated supine positions can potentially increase the error in relative body angles and body posture assessments derived consequently.

Figure 6:
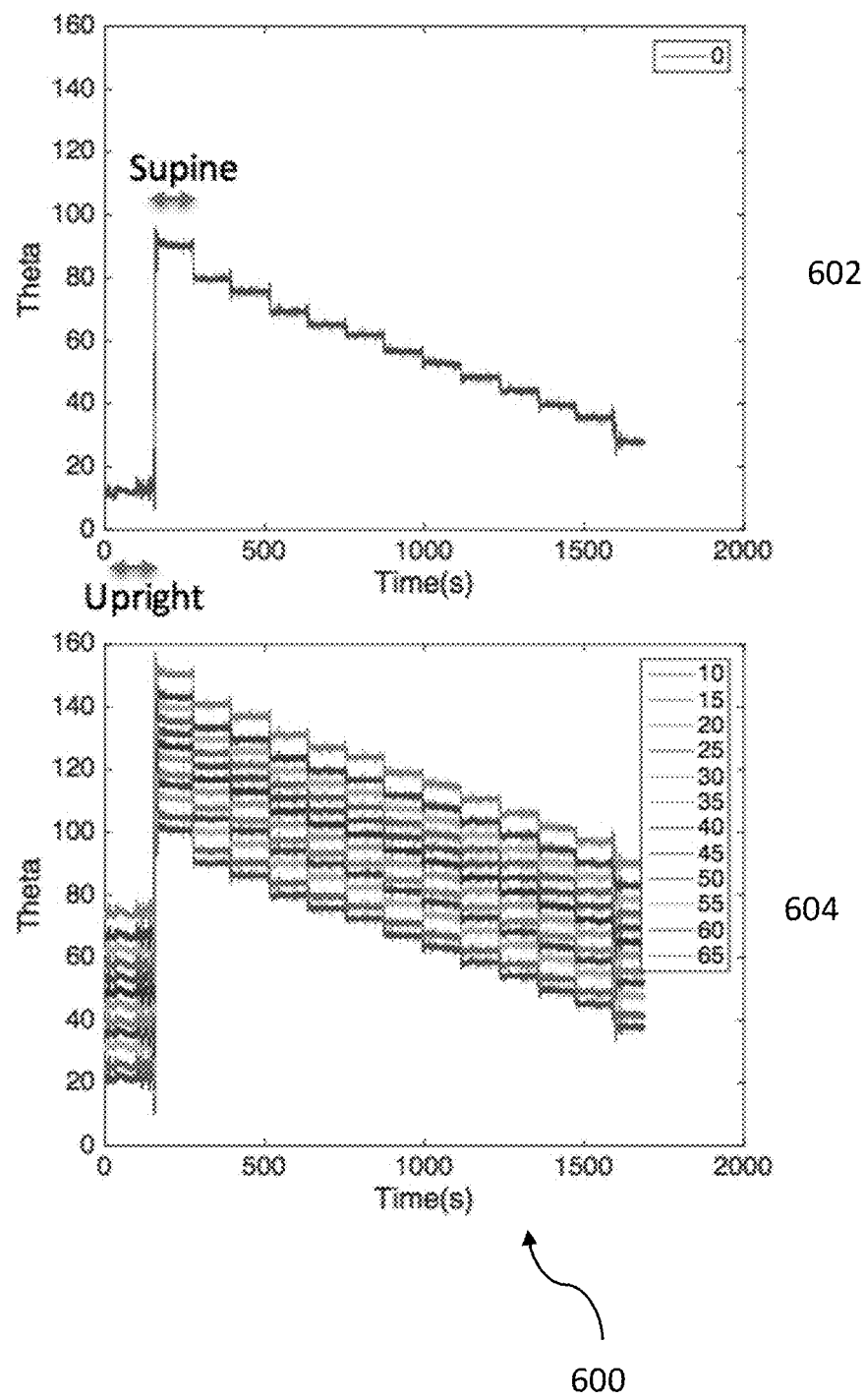
FIG. 6 illustrates calculated examples of vertical body angle ($\theta$) in a subject in a series of successive body positions by applying the Calibration in Supine Algorithm at body positions of supine (about 0°) (upper panel) as a reference, and at bed elevations of about 10°, 15°, 20°, 25°, . . . 65° (lower panel).

FIG. 6 illustrates calculated vertical body angles (θ) in one example subject carrying out a series of successive body positions. In the illustration, method 300 is used to calibrate the sensor when the subject has a body position at supine (i.e., bed elevation about 0°), and the calculated θ values are shown in upper panel 602. Accordingly, the calculated θ value is around 10° for a body position of upright and around 90° for a body position of supine. Performing calibration at 0° bed elevation is an intended use case scenario for method 300, and the resulting vertical body angles (θ) as in the upper panel can be considered as reference θ values for the comparison of use case scenario at elevated bed angles.

If method 300 is used to calibrate the sensor when the subject has a body position at any of a bed elevation of 10°, 15°, 20°, 25°, . . . and 65°, the calculated θ values are shown in lower panel 604. Performing calibration using method 300 at elevated supine positions (bed elevations of 10° thru 65°) as in lower panel 604 show errors or deviations in the calculated θ values compared to the reference θ values from supine position at 0° bed elevation (upper panel 602). In illustration 600, the higher the sensor/body elevations due to bed elevations, the greater the error of the derived vertical body angles as compared to reference body angle values obtained at 0° bed elevation. Thus, performing method 300 at an increased bed elevation may result in slight to substantial error for the determined vertical body angle (θ) depending on the amount of bed elevation. Such error may arise in method 300 when applied at bed elevations due to a deviation in the desired initial condition from 0° bed elevation or other reasons.

Indeed, calibration using method 300 at increased bed elevations may cause serious confusion of body postures. For example, depending on the amount of bed elevation and threshold values of θ set for classification of body postures (according to one embodiment, θ<30° may refer to upright; θ>65° may refer to supine; θ between 30° and 65° may refer to leaning), if method 300 is used to calibrate the sensor at increased bed elevations, an upright posture may be misclassified as leaning or supine, or a leaning posture may be misclassified as supine, for example.

Consider upper panel 602 in FIG. 6, which illustrates vertical body angle (θ) determined following calibration in supine using method 300. Under such conditions, vertical body angle (θ) of an upright subject is determined to be about 10° (not precisely 0° due, e.g., to the contours of the upper body) and vertical body angle (θ) of a supine subject about 90°. As upper panel 602 illustrates, the determined vertical body angle (θ) decreases stepwise from about 90° for the corresponding changes in bed elevation from about 0°, 10°, 15°, 20°, . . . 65°, if method 300 is used to calibrate the sensor at about 0° bed elevation (supine).

In lower panel 604, on the other hand, the accuracy in measured vertical body angle (θ) may suffer from calibration at increased bed elevation angles other than supine (i.e., 0°). For example, bottom panel 604 illustrates vertical body angles (θ) determined following calibration at each of the bed elevation angles from 10°-65° in 5° increments, and shows a discrepancy or error at each angle ranging from about 20° to about 60° in the examples shown (with reference to performing calibration at about 0° and considering an upright posture event as shown in upper panel 602). Thus, the Calibration in Supine Algorithm alone appears to be unreliable at bed elevation angles between about 10° and about 65°, and may render the resulting determination of body angles and body postures erroneous, as discussed above.

Thus, the determination of sensor elevation angle due to bed elevation may be considered in one or more embodiments as part of the sensor calibration. That is, the calibration algorithm should not assume zero bed elevation and should not simply compensate for or nullify the possible sensor elevation angle. Rather, the sensor elevation angle may be determined at any bed elevation, and the sensor device frame aligned to the body frame with reference to the ideal 0° elevation (e.g., horizontal earth plane). In one or more embodiments, the real relative position of the sensor on the body may be tracked, thereby allowing calibration even at elevated bed angles.

Figure 7:
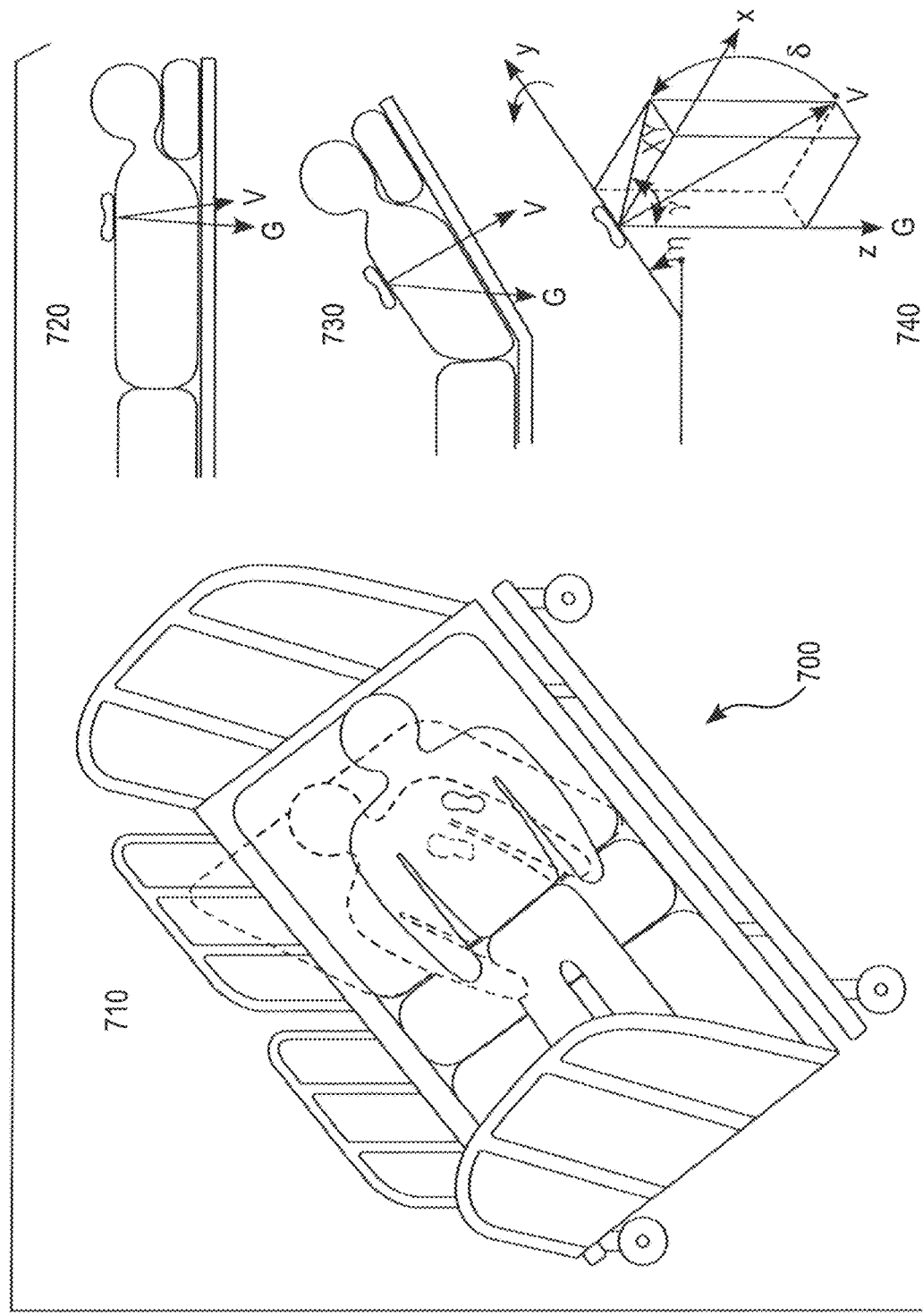
FIG. 7 illustrates schematic diagrams of a patient lying in bed at supine and elevated body positions and relationships among associated gravity and sensor vectors, a sensor elevation angle ($\eta$), and the horizontal supporting surface.

FIG. 7 illustrates schematic diagrams 700 of an example of a patient lying in bed (for example, a hospital bed) at supine and elevated body positions. The top and middle diagrams 720, 730 in the right panel show the patient attached with a sensor on the upper chest in supine and elevated body positions, respectively, and the relationships among associated gravity (G) and sensor (V) vectors are illustrated for the given body positions. The bottom diagram 740 in the right panel illustrates a representative sensor vector at an elevated body position, a gravity vector, a sensor vector rotation relative to the XY horizontal sensor plane, a sensor elevation angle (η), and the horizontal supporting surface. Utilizing the relationships shown in FIG. 7, the sensor elevation angle can be automatically derived using the sensor vector relative to the horizontal surface and gravity.

In the example shown in FIG. 7, reference numeral 710 illustrates examples of a patient attached with a sensor (on the chest according to one or more embodiments) lying on a hospital bed in supine position (the patient and bed frame are drawn in solid lines) and when part of the hospital bed is inclined to impart an upper body elevation to the patient (the bed frame and patient are drawn in dotted lines in this case). The change in bed elevation may cause a certain elevation to the frontal (XY) plane of the sensor on the subject with respect to the horizontal surface, termed the sensor elevation angle.

At 720, FIG. 7 shows a substantially supine subject (solid line representation in left panel 710) and associated sensor device. Vector $\vec{G}$ indicates gravity and vector $\vec{V}$ indicates the sensor vector. If the sensor attachment site on the subject is ideally flat with no body contour effects, the vectors $\vec{G}$ and $\vec{V}$ would be aligned. As in upper diagram 720, the sensor and gravity may not be perfectly aligned due to contours of the body. Middle diagram 730 shows a scenario in which the hospital bed is elevated, resulting in elevation of the upper body (dotted line representation in left panel 710) and the sensor vector $\vec{V}$ is shown diverging from the gravity vector $\vec{G}$. Lower diagram 740 illustrates how the sensor vector at an elevated body condition may be used to calculate the sensor elevation angle η with reference to horizontal supporting (or earth) surface by applying a rotation of angle δ to the sensor vector to align with the XY plane of the sensor vector and calculating the angle γ between the rotated sensor vector and the gravity vector.

Figure 8:
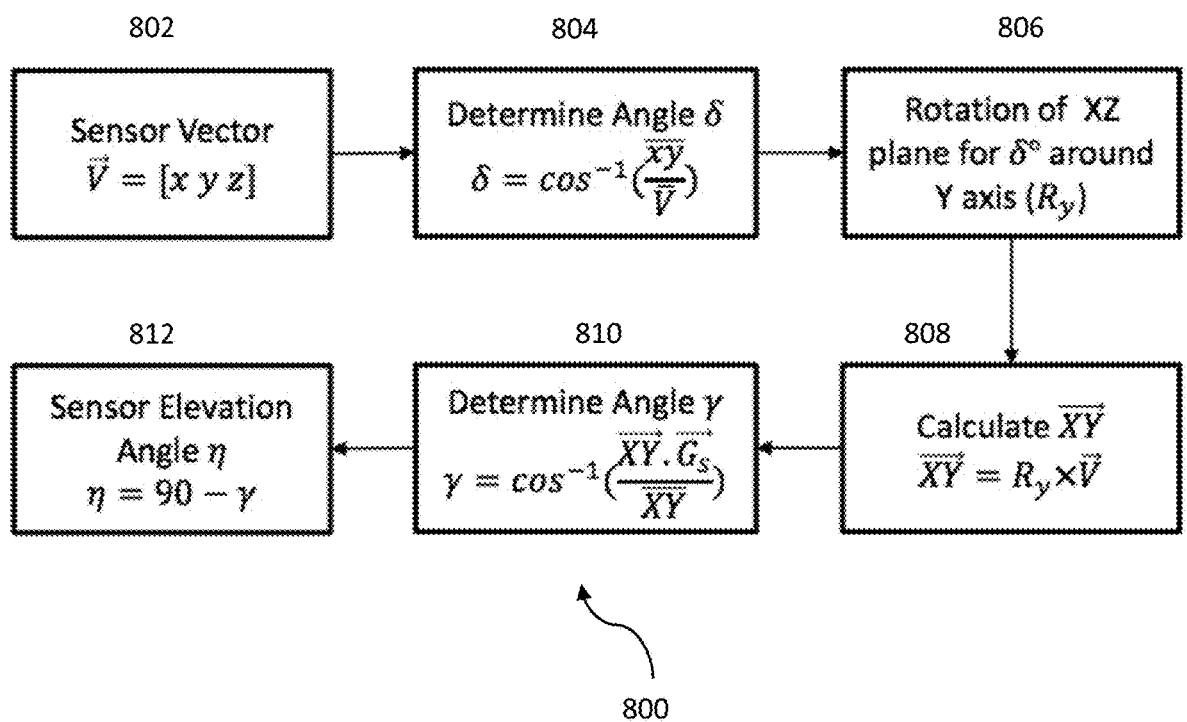
FIG. 8 illustrates a Sensor Elevation Angle Algorithm to determine a sensor elevation angle, accounting for body contour and the tilting of a supporting surface in accordance with one or more embodiments.

For a given sensor vector, a sensor elevation angle η can be determined by a Sensor Elevation Angle Algorithm 800 shown in FIG. 8. In step 802, sensor vector $\vec{V}$ may be determined by a MEMS (e.g., accelerometer) using, e.g., a process similar to that of step 302. For example, one sample or an aggregate of samples of body acceleration of the subject's body under stable supine position may be obtained from sensor device 100 as a sensor vector $\vec{V}$=[x y z] in accordance with one or more embodiments, where the sensor can be a tri-axial accelerometer and [x y z] be the acceleration values in three axes. Step 804 determines the angle δ as in equation $$\delta = \cos^{-1}\left(\frac{\overline{xy}}{V}\right),$$

where $\overline{xy}$ is the XY magnitude of sensor vector $\vec{V}$ determined by $\overline{xy}=\sqrt{x^2+y^2}$ and $V$ is the overall magnitude of sensor vector $\vec{V}$ determined by $V=\sqrt{x^2+y^2+z^2}$. Rotational matrix $R_y$ may be determined for rotating the XZ plane of the sensor vector by δ° around the Y axis in step 806. Depending on whether the rotation is applied using the left-hand-rule or the right-hand-rule and sensor configuration, the rotational matrices may differ. An example of $R_y$ can be [1 0 0; cos δ (−sin δ) 0; 0 sin δ cos δ], according to one or more embodiments. In step 808, the rotated sensor vector on XY plane $\overrightarrow{XY}$ may be determined by the product of $R_y$ and $\vec{V}$. In step 810, angle γ between the $\overrightarrow{XY}$ vector and gravity vector $\overrightarrow{G_S}$ at ideal supine position (0°) may be determined by the equation $$\gamma = \cos^{-1}\left(\frac{\overrightarrow{XY} \cdot \overrightarrow{G_S}}{\overrightarrow{XY}}\right),$$

where $\overrightarrow{G_S}$ can be [0 0 1], according to one embodiment. With the determined γ angle, the sensor elevation angle η may be determined by the equation η=90−γ in step 812. Thus, when the subject is in supine with any bed elevation, the Sensor Elevation Angle Algorithm can automatically determine the elevation angle η resulting in the sensor's XY plane due to bed elevation using the measured sensor vector.

Figure 9:
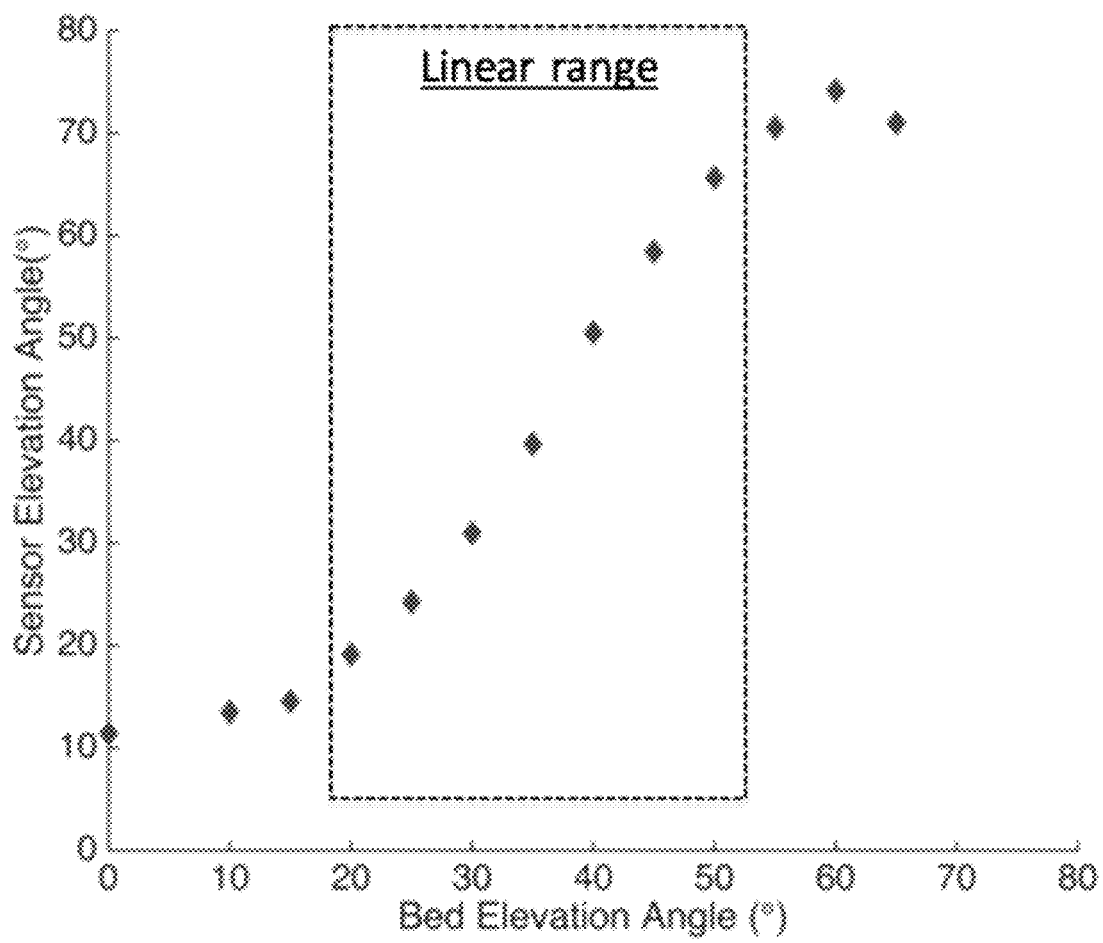
FIG. 9 illustrates a scatterplot of the determined sensor elevation angles (Y axis) for incremental changes in bed elevation angles from about 0° to about 65° (X axis) in a subject with a sensor device attached on the chest, showing a substantially linear relationship in measured sensor elevations in the middle range of input bed elevations.

FIG. 9 illustrates a scatterplot of example determined sensor elevation angles (Y axis) for incremental changes in bed elevation angles from 0° to 65° (X axis) in a subject with a sensor device attached on the chest, showing a substantially nonlinear relationship overall in the measured sensor elevations for a range of input bed elevations. The nonlinear response is evident for the incremental changes in bed elevation particularly at the lower and higher elevations, since small incremental changes in bed elevation proximity to supine and upright body positions may not produce substantial change in body elevation due to conformity of the body. As shown by the plot, a linear relationship may be possible nevertheless for a range of bed elevation angles, if the subject's body conforms well to the bed plane.

The overall sensor elevation angle response to the changes in bed elevations can vary widely among individuals influenced by variations in body contour, body mass index, sensor placement on the subject. At lower or higher bed elevation values outside the linear range, the sensor elevation angle may vary drastically in a more nonlinear manner, for example due to slouching or a sensor placement on a flabby muscle mass.

Figure 10:
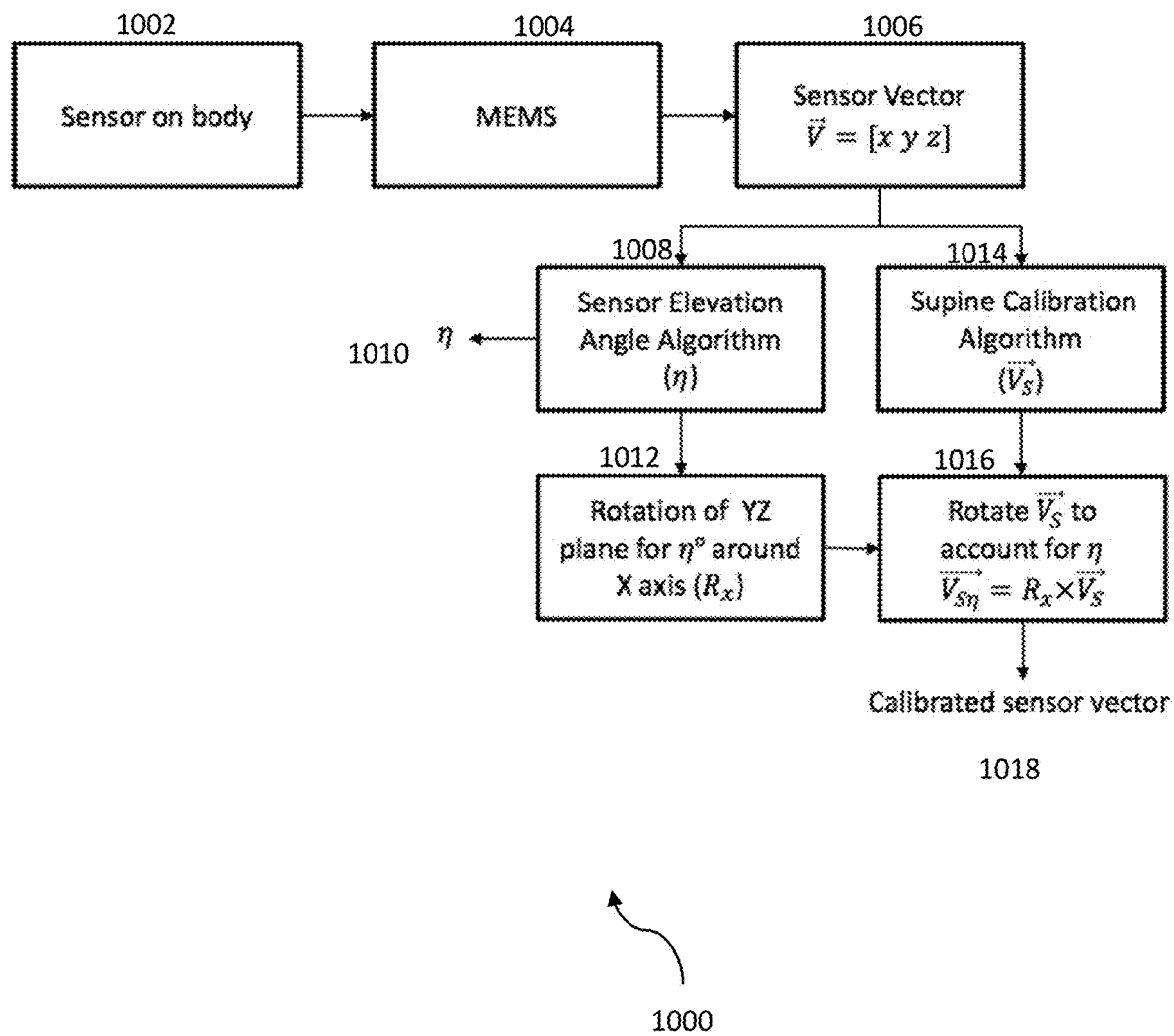
FIG. 10 illustrates a method of performing a calibration when the user is in supine with or without sensor/body elevation using a Calibration with a Sensor Angle Algorithm that utilizes both the Sensor Elevation Angle Algorithm and the Calibration in Supine Algorithm according to one or more embodiments.

FIG. 10 illustrates a method of performing a calibration when the subject is in supine, with or without sensor/body elevation, using a Calibration with Sensor Angle Algorithm 1000 that may utilize both Sensor Elevation Angle Algorithm 800 and Calibration in Supine Algorithm 300 according to one or more embodiments. In step 1002, sensor device 100 may be attached to the subject, and in step 1004, a MEMS associated with sensor device 100 may be activated. In step 1006, a sensor vector $\vec{V}$ may be determined from the MEMS, for example using a process similar to that of steps 302 or 802.

In step 1008, Sensor Elevation Angle Algorithm 800 may be performed to determine the sensor elevation angle $\eta$ using sensor vector $\vec{V}$. The sensor elevation angle $\eta$ can be output as in step 1010. In step 1012, with the calculated sensor elevation angle $\eta$, rotational matrix $R_x$ may be determined for rotating the YZ plane of the sensor vector for $\eta°$ around the X axis.

In step 1014, Calibration in Supine Algorithm 300 may be performed using sensor vector $\vec{V}$ to determine calibrated sensor vector $\vec{V}_S$. In step 1016, calibrated sensor vector $\vec{V}_S$ may be rotated using rotational matrix $R_x$ to obtain a calibrated sensor vector $\vec{V}_{S\eta} = R_x \times \vec{V}_S$ that now accounts for sensor elevation angle $\eta$. The calibrated sensor vector $\vec{V}_{S\eta}$ may be output in step 1018 and used for processing of physiological and physical assessment including vertical body angle and posture, respiration, core body activity and fall detection, for example. Thus, Calibration with Sensor Angle Algorithm 1000 allows calibration of a sensor when the patient is lying on a supporting surface such as a bed, with or without elevation, and overcomes the limitations of Calibration in Supine Algorithm 300 used alone, by performing an additional rotation accounting for the sensor elevation.

As seen, according to one or more embodiments of a system, device and method, Calibration with Sensor Angle Algorithm 1000 allows performing calibration of a sensor on, e.g., a subject lying supine in bed, with or without tilting of the supporting surface, by automatically determining the sensor elevation angle (via Sensor Elevation Angle Algorithm 800) and calibrating the sensor 100 in conjunction with Calibration in Supine Algorithm 300 using an initial sensor vector. Thus method 1000 incorporates methods 300 and 800 and performs an additional rotation for true calibration of the sensor. Overall, method 1000 quantifies the sensor elevation angle due to body contour or bed/body elevation accurately, aligns the sensor to the gravity vector with respect to the horizontal plane, allows accurate tracking of the true relative position of the sensor on the body, and allows calibration at elevated bed angles as well as supine.

Figure 11:
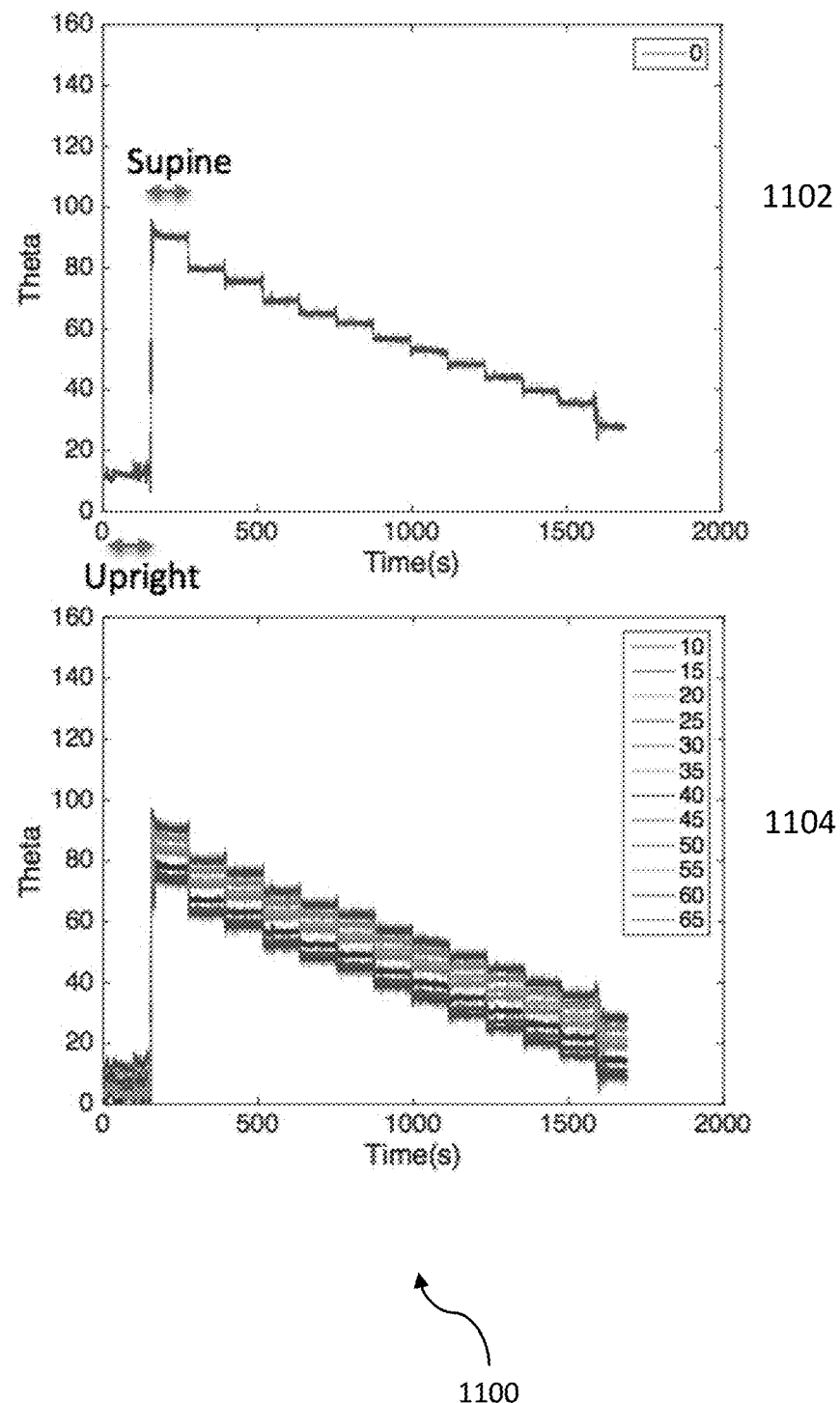
FIG. 11 illustrates calculated examples of vertical body angle ($\theta$) in a subject carrying out a series of successive body positions by applying the Calibration in Supine Algorithm at body positions of supine (about 0°) (upper panel), and applying the Calibration with a Sensor Angle Algorithm at bed elevations of about 10°, 15°, 20°, 25°, . . . 65° (lower panel) according to one or more embodiments.

FIG. 11 illustrates calculated examples 1100 of vertical body angle (θ) in a subject carrying out a series of successive body positions by applying Calibration in Supine Algorithm 300 at body positions of supine (about 0°) (upper panel 1102) as a reference for comparison, and applying Calibration with a Sensor Angle Algorithm 1000 at bed elevations at about 10°, 15°, 20°, 25°, . . . 65° (lower panel 1104) according to one or more embodiments. Comparison of vertical body angle values in lower panel 1104 of FIG. 11 to lower panel 604 of FIG. 6 (obtained with Calibration in Supine Algorithm 300) indicates that Calibration with a Sensor Angle Algorithm 1000 may substantially reduce error in θ values when compared with applying Calibration in Supine Algorithm 300 for elevated bed angles.

For example, upper panel 1102 shows vertical body angles (θ) obtained with, e.g., Calibration in Supine Algorithm 300 at 0° bed elevation as an intended use case scenario, which may be considered as reference θ values for the comparison of use case scenario at elevated bed angles. Accordingly, the vertical body angle θ is about 10° at upright and 90° at supine with 0° bed elevation. θ values show stepwise decreases for stepwise increase in bed elevation. The data in upper panel 1102 of FIG. 11 is comparable to the data in upper panel 602 of FIG. 6.

Lower panel 1104 shows vertical body angles (θ) obtained with calibration performed using Calibration with a Sensor Angle Algorithm 1000, at each of the bed elevation angles 10°-65° in 5° increments. As seen particularly by contrast with lower panel 604, lower panel 1104 shows that Calibration with a Sensor Angle Algorithm 1000 may help to eliminate inaccuracies in vertical body angle (θ) while performing calibration at higher bed/body elevations. In particular, the variation of vertical body angle (θ) across various elevation angles of calibration shows a reasonable error margin of only about 10 degrees for all calibrations at bed elevations from 10°-65° in 5° increments with respect to the ideal reference (upper panel 1102). This contrasts with the errors of about 20° to about 60° shown in lower panel 604.

Figure 12:
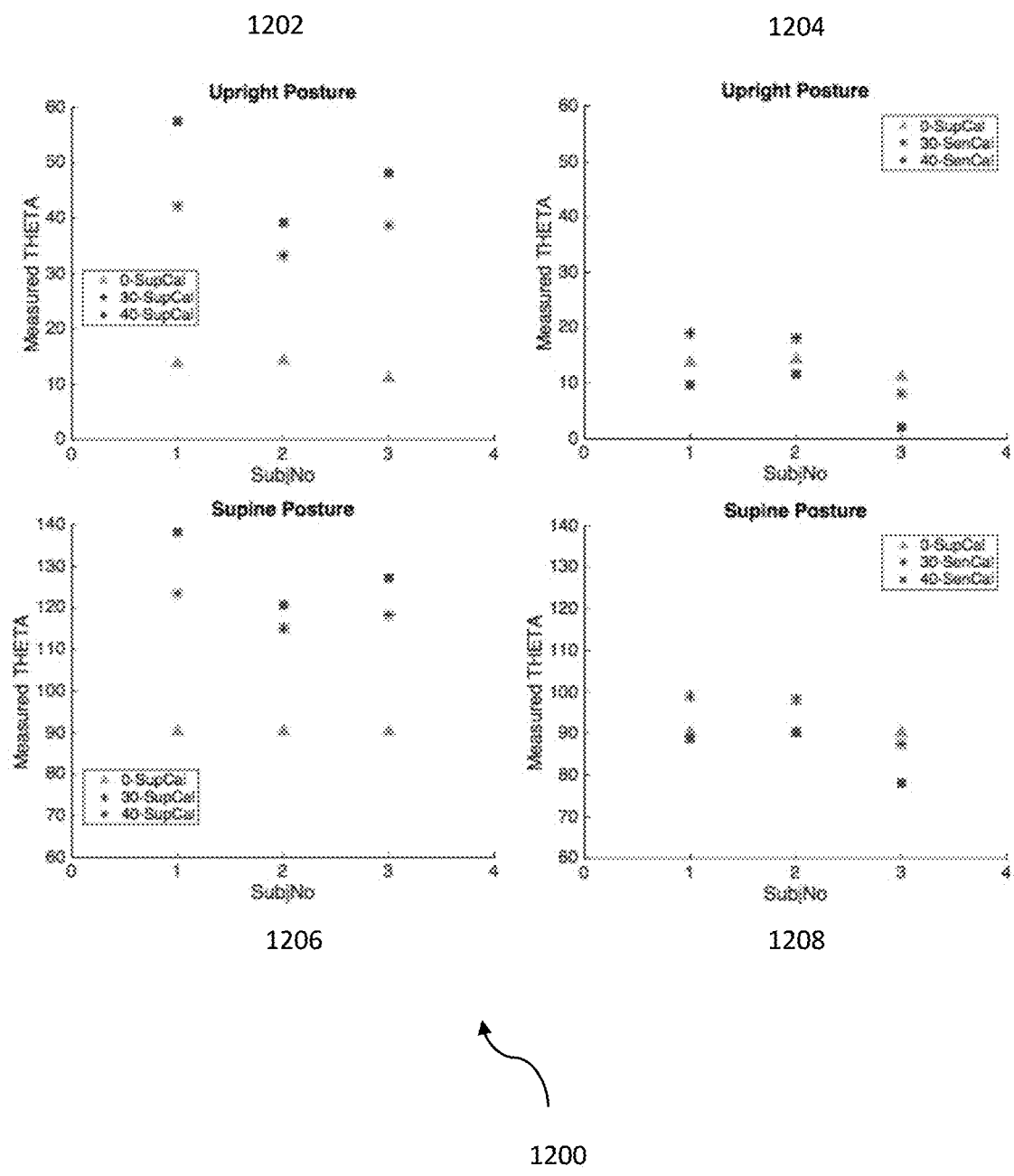
FIG. 12 shows a comparison of vertical body angle ($\theta$) measurements calculated for upright posture (top row) and supine posture (bottom row) using the Calibration in Supine Algorithm (denoted as SupCal) (left column) vs. the Calibration with a Sensor Angle Algorithm (denoted as SenCal) (right column).

Vertical body angles (θ) calculated in one subject for a series successive body positions by applying calibration at each of the bed elevations from 0° through 65° are shown in FIG. 11. FIG. 12 now illustrates how the calculated θ angles vary in multiple subjects among the calibration methods 300 and 1000. FIG. 12 shows a comparison 1200 of vertical body angle (θ) measurements calculated in 3 subjects as an example for upright posture (top row) and supine posture (bottom row) using Calibration in Supine Algorithm 300 (denoted as SupCal) (left column) vs. Calibration with a Sensor Angle Algorithm 1000 (denoted as SenCal) (right column), illustrating the reduction of substantial error in θ values at elevated bed angles of 30° and 40° using SenCal with reference to 0° SupCal that indicates improved accuracy of determining upright posture and supine posture after calibration at such elevated bed angles.

Panel 1202 shows measured vertical angles (θ) at upright posture in subjects 1, 2 and 3 by performing calibration at bed elevation angles 0°, 30°, and 40° using Calibration in Supine Algorithm 300 (SupCal). Performing calibration at 0° bed elevation is an intended use case for SupCal resulting in the measured θ of around 10° for upright position in all 3 subjects. On the other hand, calibration with SupCal at around 30° and 40° bed elevations may provide θ values above 30° as shown (the example of subject 1 calibrated with SupCal at 40° bed elevation shows θ close to 60° at upright position), which can be incorrectly identified as leaning position compared to the upright position expected to be identified. Thus, performing calibration using SupCal at bed elevations may provide θ values with substantial error compared to the 0° reference case depending upon the bed elevation level. By contrast, in panel 1204, Calibration with a Sensor Angle Algorithm 1000 (SenCal) at 30° and 40° bed elevation show error in measured θ no more than about 10° in each subject for upright position, illustrating the reduction of substantial error in θ values for calibration at elevated bed angles of 30° and 40° and improved accuracy of determining upright posture using the SenCal algorithm 1000.

Panel 1206 shows measured vertical angles (θ) at supine posture in subjects 1, 2 and 3 by performing calibration at bed elevation angles 0°, 30°, and 40° using Calibration in Supine Algorithm 300 (SupCal). Performing calibration at 0° bed elevation is an intended use case for SupCal resulting in the measured θ as 90° for supine posture in all 3 subjects. On the other hand, calibration with SupCal at 30° and 40° bed elevations may provide θ values above 110° as shown (the example of subject 1 calibrated with SupCal at 40° bed elevation shows θ close to 140° at upright position compared to ideal 90°, resulting an error of about 50°). By contrast, in panel 1208, Calibration with a Sensor Angle Algorithm 1000 (SenCal) at 30° and 40° bed elevation show error in measured θ no more than about 10° in each subject for supine position, illustrating the reduction of substantial error in θ values at elevated bed angles of 30° and 40° using the SenCal algorithm 1000.

Figure 13:
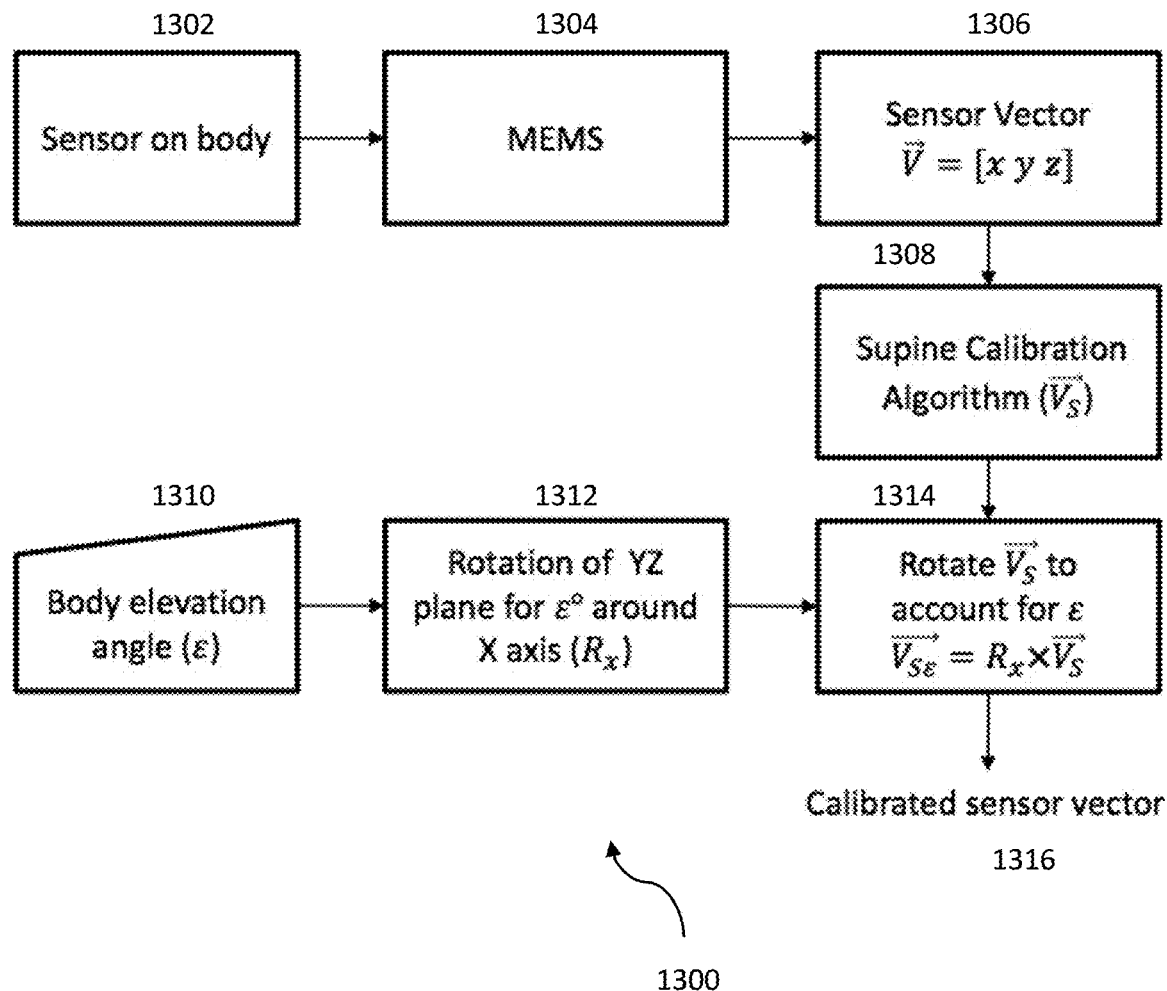
FIG. 13 shows a method of performing calibration of a subject in supine with and without body elevation angle (e.g., bed elevation angle) using a Calibration with a Body Angle Algorithm that utilizes user input of body angle (elevation) and the Calibration in Supine Algorithm according to one or more embodiments.

FIG. 13 shows a method of performing calibration of a subject in supine with and without body elevation angle (e.g., bed elevation angle) using a Calibration with a Body Angle Algorithm 1300 that utilizes user input of body angle (or bed elevation read out from a hospital bed indicator, for example, which may be mounted or otherwise operably coupled to the bed, including remotely) and Calibration in Supine Algorithm 300 according to one or more embodiments. In step 1302, sensor device 100 may be attached to the subject. In step 1304, a MEMS (e.g., accelerometer) associated with sensor device 100 may be activated. In step 1306, a sensor vector $\vec{V}$ may be determined from the MEMS, for example using a process similar to that of steps 302, 802, or 1006. In step 1308, Calibration in Supine Algorithm 300 may be performed using sensor vector $\vec{V}$ to determine intermediate calibrated sensor vector $\vec{V}_S$.

In step 1310, a body elevation angle ε may be input manually (e.g., via a keypad input provided on sensor device 100 or a user interface application on a smart phone or tablet, or by providing a signal remotely) or automatically (e.g., by electrically or otherwise providing a bed elevation setting). In step 1312, with the user input on body elevation angle ε, a rotational matrix $R_x$ may be determined representing a rotation of the YZ plane of the sensor vector for ε° around the X axis. Depending on whether the rotation is applied using the left-hand-rule or right-hand-rule and sensor configuration, the rotational matrices may differ. An example of $R_x$ can be [1 0 0; 0 cos ε (−sin ε); 0 sin ε cos ε], according to one embodiment. In step 1314, the intermediate calibrated sensor vector $\vec{V}_S$ obtained in step 1308 may be rotated by rotational matrix $R_x$ to obtain the final calibrated sensor vector $\vec{V}_{Sε}$ that accounts for the body elevation angle ε by the equation $\vec{V}_{Sε} = R_x \times \vec{V}_S$. The final calibrated sensor vector may be output by the step 1316 which may be used for processing of physiological and physical assessment including vertical body angle and posture, respiration, core body activity and for fall detection, for example.

Figure 14:
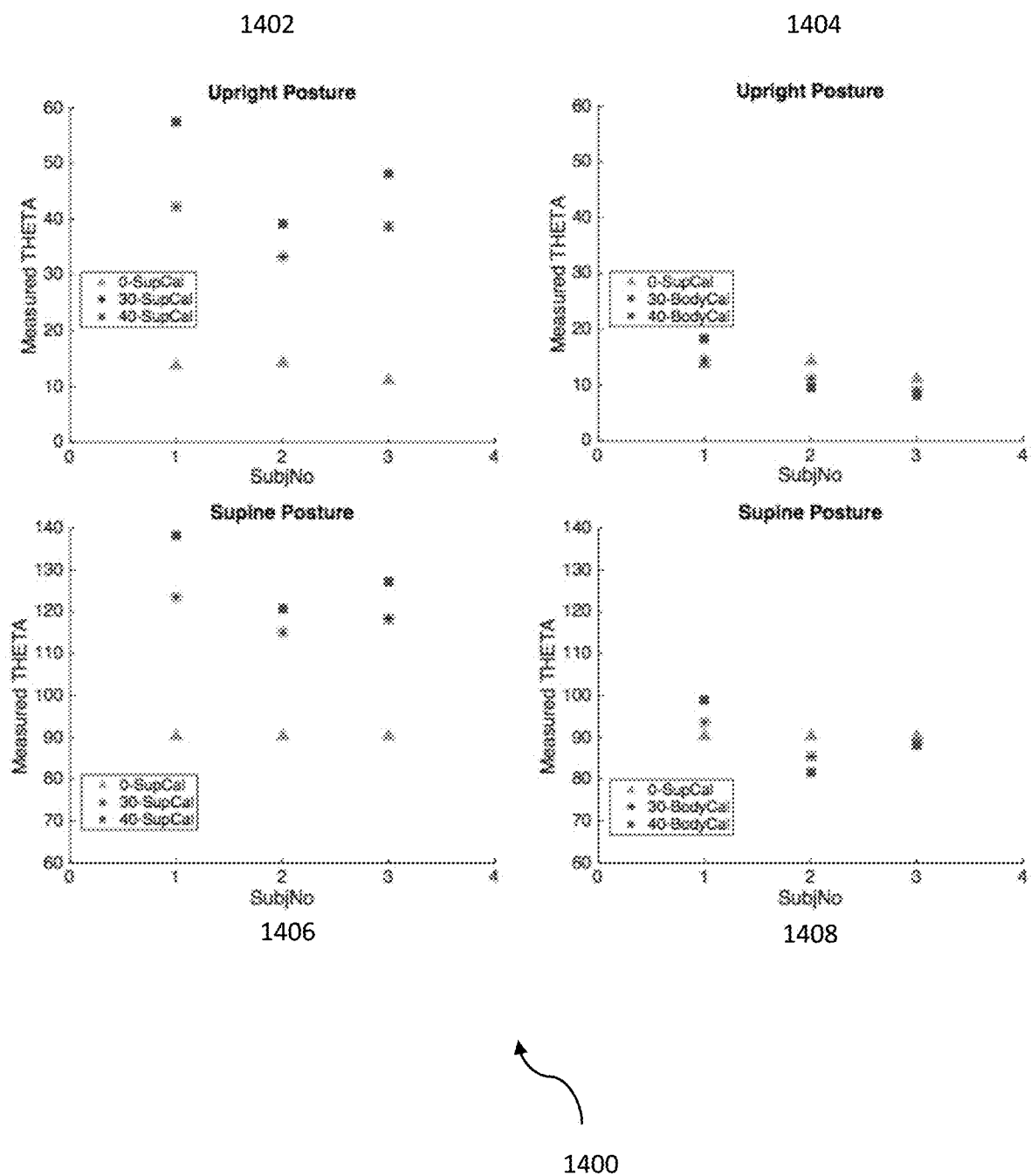
FIG. 14 shows a comparison of vertical body angle ($\theta$) determined for upright posture (top row) and supine posture (bottom row) using the Calibration in Supine Algorithm (denoted as SupCal) (left column) vs the Calibration with a Body Angle Algorithm (denoted as BodyCal) (right column).

FIG. 14 illustrates how the calculated angles may vary in multiple subjects calibration methods 300 and 1300. FIG. 14 shows a comparison 1400 of vertical body angle (θ) measurements determined in 3 subjects as examples for upright posture (top row) and supine posture (bottom row) using Calibration in Supine Algorithm 300 (denoted as SupCal) (left column) vs Calibration with a Body Angle Algorithm 1300 (denoted as BodyCal) (right column), illustrating the reduction of substantial error in θ values at elevated bed angles of 30° and 40° using BodyCal with reference to 0° SupCal, indicating improved accuracy of determining upright posture and supine posture after calibration at such elevated bed angles.

Panel 1402 (as in panel 1202) shows examples of measured vertical angles (θ) at upright posture in subjects 1, 2 and 3 by performing calibration at bed elevation angles 0°, 30°, and 40° using Calibration in Supine Algorithm 300 (SupCal). Performing calibration at around 0° bed elevation is the intended use case for SupCal resulting in the measured θ of around 10° for upright position in all 3 subjects. On the other hand, calibration with SupCal at 30° and 40° bed elevations may provide θ values above 30° as shown (the example of subject 1 calibrated with SupCal at 40° bed elevation shows θ close to 60° at upright position), which can be incorrectly identified as leaning position compared to the upright position expected to be identified. Thus, performing calibration using SupCal at bed elevations may provide θ values with substantial error compared to the 0° reference case depending upon the bed elevation level. By contrast, in panel 1404, Calibration with a Body Angle Algorithm 1300 (BodyCal) at 30° and 40° bed elevation show error in measured θ of no more than about 10° in each subject for upright position, illustrating the reduction of substantial error in θ values at elevated bed angles of 30° and 40° and improved accuracy of determining upright posture using the BodyCal algorithm 1300.

Panel 1406 shows (as in panel 1206) examples of measured vertical angles (θ) at supine posture in subjects 1, 2 and 3 by performing calibration at bed elevation angles 0°, 30°, and 40° using Calibration in Supine Algorithm 300 (SupCal). Performing calibration at 0° bed elevation is the intended use case for SupCal resulting in the measured θ as 90° for supine posture in all 3 subjects. On the other hand, calibration with SupCal at 30° and 40° bed elevations may provide θ values above 110° as shown (the example of subject 1 calibrated with SupCal at 40° bed elevation shows θ close to 140° at upright position compared to ideal 90° resulting an error of 50°). By contrast, in panel 1408, Calibration with a Body Angle Algorithm 1300 (BodyCal) at 30° and 40° bed elevation show error in measured θ of no more than about 10° in each subject for supine position, illustrating the reduction of substantial error in θ values at elevated bed angles of 30° and 40° using the BodyCal algorithm 1300.

Performing calibration using the methods 300, 1000 or 1300 may include the subject lying supine on a horizontal supporting surface such as a bed without or with any tilting. It should be noted that one or more steps of FIG. 3, FIG. 8, FIG. 10, and/or FIG. 13, as in all methods disclosed herein, may be combined and/or performed in a modified order, and/or omitting one or more steps.

The sensor device described in this disclosure may include or take the form of a wearable patch sensor in a fully disposable or semi-disposable form according to one or more embodiments, and/or a reusable electronic device in one or more embodiments. This sensor device may be connected/paired via wires or wirelessly to one or more external devices, including but not limited to a smartphone, tablet, or relay. In one or more embodiments, machine-readable signal features may be processed using an on-board sensor processor, application, and memory and produce human- and/or machine-readable outputs, including but not limited to the signal features described herein, then encrypted and transmitted via a BLE link to an external relay for further analysis, storage, and/or viewing. In one or more embodiments, the sensor signals or signal features may be processed in a processor and memory, then encrypted and transmitted via a BLE link to an external relay and/or cloud, where processing of those signals or features may be carried out to determine subject posture, core body activity, and/or other information.

A method, device and system for determining sensor elevation angle and performing sensor calibration has been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or calculator-readable medium. The software application may provide instructions that enable the processor to perform one or more of the functions described herein.

Furthermore, one or more embodiments may take the form of a calculator program product accessible from a calculator-usable or calculator-readable medium providing program code for use by or in connection with a calculator or any instruction execution system. For the purposes of this description, a calculator-usable or calculator-readable medium can be any apparatus that can contain, store, communicate, propagate, or transport the program for use by or in connection with the instruction execution system, apparatus, or device.

The medium may be an electronic, magnetic, optical, electromagnetic, infrared, semiconductor system (or apparatus or device), or a propagation medium. Examples of a calculator-readable medium include a semiconductor or solid state memory, magnetic tape, a removable calculator diskette, a random access memory (RAM), a read-only memory (ROM), a rigid magnetic disk, and an optical disk. Current examples of optical disks include DVD, compact disk-read-only memory (CD-ROM), and compact disk-read/write (CD-R/W).

As suggested above, although one or more embodiments are disclosed in which sensor device 100 may provide information wirelessly, sensor device 100 may include, additionally or alternatively, structure capable of transmitting information via wires. For example, sensor device 100 may have one or more ports to connect wires via which information may be transmitted. Further, although a single sensor device 100 is described by way of example, one or more of the disclosed functions may be performed by one or more other sensor devices, whether wearable or unworn, and/or devices located externally of the subject.

As indicated above, the foregoing description is presented to enable one of ordinary skill in the art to make and use the disclosed embodiments and modifications thereof, and is provided in the context of a patent application and its requirements.

Various modifications to the disclosed embodiments and the principles and features described herein will be readily apparent to those of ordinary skill in the art. Thus, the present disclosure is not intended to limit the invention to the embodiments shown; rather, the invention is to be accorded the widest scope consistent with the principles and features described herein.

What is claimed is:

1. A method of calibrating a sensor associated with a subject, comprising:

producing, by the sensor, a sensor vector $\vec{V}$ associated with a body acceleration of the subject relative to a gravity vector;

calibrating the sensor vector $\vec{V}$, including:

processing the sensor vector $\vec{V}$ with the subject at a first elevation angle relative to a reference to produce a first calibrated sensor vector $\vec{V}_S$, wherein the processing of the sensor vector includes:

determining an angle $\alpha$ and applying rotational matrix $R_1$ to the sensor vector $\vec{V}$, wherein the rotational matrix $R_1$ is an XY rotation for $\alpha°$ around a Z axis, determining an angle $\beta$ and applying rotational matrix $R_3$ to the sensor vector $\vec{V}$, wherein the rotational matrix $R_3$ is a YZ rotation for $\beta°$ around an X axis, obtaining user input on an orientation of the sensor with reference to a midline of the body and determining an ideal upright sensor vector $\vec{V}_u$, determining rotational matrix $R_s$ by the product of the rotational matrix $R_3$ and the rotational matrix $R_1$, wherein the rotational matrix $R_s$ is an intermediate rotational matrix, applying the rotational matrix $R_s$ rotation to the ideal upright sensor vector $\vec{V}_u$ to obtain a rotated ideal upright sensor vector $\overrightarrow{V'_u}$, and determining an angle $\zeta$ using $\overrightarrow{V'_u}$ and applying the rotational matrix $R_2$ to the sensor vector $\vec{V}$ to obtain the first calibrated sensor vector $\vec{V}_S$ wherein the rotational matrix $R_2$ includes an XY rotation for $\zeta°$ around the Z axis;

determining a second elevation angle $\eta$ associated with elevation of the subject relative to the reference, wherein the determining of the second elevation angle $\eta$ includes:

determining an angle $\delta$ and rotational matrix $R_y$, wherein the rotational matrix $R_y$ is an XZ rotation for $\delta°$ around a Y axis, applying the rotational matrix $R_y$ rotation to the sensor vector $\vec{V}$ to obtain $\overrightarrow{XY}$, wherein $\overrightarrow{XY}$ is the rotated vector on an XY plane, determining an angle $\gamma$ using reference to $\overrightarrow{XY}$ and an ideal gravity vector on supine $\vec{G}_s$, and obtaining the sensor elevation angle $\eta$ as a function of $\gamma$;

determining rotational matrix $R_x$, by rotating an YZ plane of the sensor vector $\vec{V}$ for $\eta°$ around the X axis;

calculating a second calibrated sensor vector $\vec{V}_{S\eta}$ as a function of $R_x$ and the first calibrated sensor vector $\vec{V}_S$; and determining a physiological or physical assessment of the subject using the second calibrated sensor vector $\vec{V}_{S\eta}$.

2. The method of claim 1, wherein:

the angle $\alpha$ is an arccosine of ratio of a y component to a magnitude in an XY plane of the sensor vector $\vec{V}$;

the angle $\beta$ is a function of arccosine of a ratio of the magnitude in the XY plane to an overall magnitude of the sensor vector $\vec{V}$; and the angle ζ is an arccosine of the ratio of a y component to the magnitude in the XY plane of the rotated ideal upright sensor vector $\vec{V}'_u$.

3. The method of claim 1, wherein
the angle δ is an arccosine of the ratio of the magnitude in the XY plane to an overall magnitude of the sensor vector $\vec{V}$; and
the angle γ is an arccosine of the ratio of a dot product of $\overrightarrow{XY}$ and $\vec{G}_s$ to the magnitude of $\overrightarrow{XY}$.

4. The method of claim 1, wherein the determination of the second elevation angle η includes receiving an input of a body elevation angle ε of the subject.

5. A system to calibrate a sensor associated with a subject, comprising:
a processor; and
a memory device coupled to the processor, wherein the memory device includes an application that, when executed by the processor, causes the processor to:
determine a sensor vector $\vec{V}$ associated with body acceleration of the subject relative to a gravity vector;
calibrate the sensor vector $\vec{V}$, including:
processing the sensor vector $\vec{V}$ with the subject at a first elevation angle relative to a reference to produce a first calibrated sensor vector $\vec{V}_s$, wherein the processing of the sensor vector includes:
determining an angle α and applying rotational matrix $R_1$ to the sensor vector $\vec{V}$, wherein the rotational matrix $R_1$ is an XY rotation for α° around a Z axis,
determining an angle β and applying rotational matrix $R_3$ to the sensor vector $\vec{V}$, wherein the rotational matrix $R_3$ is a YZ rotation for β° around an X axis,
obtaining user input on an orientation of the sensor with reference to a midline of the body and determining an ideal upright sensor vector $\vec{V}_u$,
determining rotational matrix $R_s$ by the product of the rotational matrix $R_3$ and the rotational matrix $R_1$, wherein the rotational matrix $R_s$ is an intermediate rotational matrix,
applying the rotational matrix $R_s$ rotation to the ideal upright sensor vector $\vec{V}_u$, to obtain a rotated ideal upright sensor vector $\vec{V}'_u$, and
determining an angle ζ using $\vec{V}'_u$ and applying rotational matrix $R_2$ to the sensor vector $\vec{V}$ to obtain the first calibrated sensor vector $\vec{V}_s$, wherein the rotational matrix $R_2$ includes an XY rotation for ζ° around the Z axis;
determining a second elevation angle η associated with elevation of the subject relative to the reference, wherein the determining of the second elevation angle η includes:
determining an angle δ and rotational matrix $R_y$, wherein the rotational matrix $R_y$ is an XZ rotation for δ° around a Y axis,
applying the rotational matrix $R_y$ rotation to the sensor vector $\vec{V}$ to obtain $\overrightarrow{XY}$, wherein $\overrightarrow{XY}$ is the rotated vector on an XY plane,
determining an angle γ using reference to $\overrightarrow{XY}$ and an ideal gravity vector on supine $\vec{G}_s$, and
obtaining the sensor elevation angle η as a function of γ;
determining rotational matrix $R_x$, by rotating an YZ plane of the sensor vector $\vec{V}$ for η° around the X axis;
calculating a second calibrated sensor vector $\vec{V}_{s\eta}$ as a function of $R_x$, and the first calibrated sensor vector $\vec{V}_s$; and
determine a physiological or physical assessment of the subject using the second calibrated sensor vector $\vec{V}_{s\eta}$.

6. The system of claim 5, wherein:
the angle α is an arccosine of ratio of a y component to a magnitude in an XY plane of the sensor vector $\vec{V}$;
the angle β is a function of arccosine of a ratio of the magnitude in the XY plane to an overall magnitude of the sensor vector $\vec{V}$; and
the angle ζ is an arccosine of the ratio of a y component to the magnitude in the XY plane of the rotated ideal upright sensor vector $\vec{V}'_u$.

7. The system of claim 5, wherein
the angle ζ is an arccosine of the ratio of the magnitude in the XY plane to an overall magnitude of the sensor vector $\vec{V}$; and
the angle γ is an arccosine of the ratio of a dot product of $\overrightarrow{XY}$ and $\vec{G}_s$ to the magnitude of $\overrightarrow{XY}$.

8. The system of claim 5, wherein the determination of the second elevation angle η includes receiving an input of a body elevation angle ε of the subject.

9. A sensor device, comprising:
one or more sensors;
a structure configured to support the one or more sensors for attachment to the subject;
a processor; and
a memory device coupled to the processor, wherein the memory device includes an application that, when executed by the processor, causes the processor to:
determine a sensor vector $\vec{V}$ associated with body acceleration of the subject relative to a gravity vector;
calibrate the sensor vector $\vec{V}$, including:
calibrating the sensor vector $\vec{V}$ with the subject at a first elevation angle relative to a reference to produce a first calibrated sensor vector $\vec{V}_s$, wherein the processing of the sensor vector includes:
determining an angle α and applying rotational matrix $R_1$ to the sensor vector $\vec{V}$, wherein the rotational matrix $R_1$ is an XY rotation for α° around a Z axis,
determining an angle β and applying rotational matrix $R_3$ to the sensor vector $\vec{V}$, wherein the rotational matrix $R_3$ is a YZ rotation for β° around an X axis,
obtaining user input on an orientation of the sensor with reference to a midline of the body and determining an ideal upright sensor vector $\vec{V}_u$,
determining rotational matrix $R_s$ by the product of the rotational matrix $R_3$ and the rotational matrix $R_1$, wherein the rotational matrix $R_s$ is an intermediate rotational matrix,
applying the rotational matrix $R_s$ rotation to the ideal upright sensor vector $\vec{V}_u$ to obtain a rotated ideal upright sensor vector $\vec{V}'_u$, and
determining an angle ζ using $\vec{V}'_u$ and applying rotational matrix $R_2$ to the sensor vector $\vec{V}$ to obtain the first calibrated sensor vector $\vec{V}_S$, wherein the rotational matrix $R_z$ includes an XY rotation for $\zeta°$ around the Z axis;

determining a second elevation angle $\eta$ associated with elevation of the subject relative to the reference, wherein the determining of the second elevation angle $\eta$ includes:

determining an angle $\delta$ and rotational matrix $R_y$, wherein the rotational matrix $R_y$ is an XZ rotation for $\delta°$ around a Y axis, applying the rotational matrix $R_y$ rotation to the sensor vector $\vec{V}$ to obtain $\overrightarrow{XY}$, wherein $\overrightarrow{XY}$ is the rotated vector on an XY plane, determining an angle $\gamma$ using reference to $\overrightarrow{XY}$ and an ideal gravity vector on supine $\vec{G}_s$, and obtaining the sensor elevation angle $\eta$ as a function of $\gamma$;

determining rotational matrix $R_x$ by rotating an YZ plane of the sensor vector $\vec{V}$ for $\eta°$ around the X axis;

calculating a second calibrated sensor vector $\vec{V}_{S\eta}$ as a function of $R_x$ and the first calibrated sensor vector $\vec{V}_S$; and determine a physiological or physical assessment of the subject using the second calibrated sensor vector $\vec{V}_{s\eta}$.

10. The sensor device of claim 9, wherein:

the angle $\alpha$ is an arccosine of ratio of a y component to a magnitude in an XY plane of the sensor vector $\vec{V}$;

the angle $\beta$ is a function of arccosine of a ratio of the magnitude in the XY plane to an overall magnitude of the sensor vector $\vec{V}$; and the angle $\zeta$ is an arccosine of the ratio of a y component to the magnitude in the XY plane of the rotated ideal upright sensor vector $\overrightarrow{V'_u}$.

11. The sensor device of claim 9, wherein the angle $\delta$ is an arccosine of the ratio of the magnitude in the XY plane to an overall magnitude of the sensor vector $\vec{V}$; and the angle $\gamma$ is an arccosine of the ratio of a dot product of $\overrightarrow{XY}$ and $\vec{G}_s$ to the magnitude of $\overrightarrow{XY}$.

12. The sensor device of claim 9, wherein the determination of the second elevation angle $\eta$ includes receiving an input of a body elevation angle $\varepsilon$ of the subject.

13. The sensor device of claim 9, wherein the structure comprises a patch form factor.

14. The sensor device of claim 13, wherein the structure comprises an adhesive configured to be removably attached to the subject.

15. The sensor device of claim 9, wherein the structure comprises an adhesive configured to be removably attached to the subject.

16. The sensor device of claim 9, further comprising a wireless transmitter configured to store or transmit the determined second elevation angle $\eta$.

* * * * *